United States Patent
Kinoshita et al.

(10) Patent No.: US 10,041,137 B2
(45) Date of Patent: Aug. 7, 2018

(54) HIGH MANNOSE PROTEINS AND METHODS OF MAKING HIGH MANNOSE PROTEINS

(75) Inventors: Carol M. Kinoshita, Bedford, MA (US); Prashant Mishra, Troy, MI (US); Marianne Borowski, Winthrop, MA (US); Peter Francis Daniel, Natick, MA (US)

(73) Assignee: SHIRE HUMAN GENETIC THERAPIES, INC., Cambridge, MA (US)

(*) Notice: Subject to any disclaimer, the term of this patent is extended or adjusted under 35 U.S.C. 154(b) by 0 days.

(21) Appl. No.: 11/581,979

(22) Filed: Oct. 17, 2006

(65) Prior Publication Data

US 2007/0031945 A1   Feb. 8, 2007

Related U.S. Application Data

(62) Division of application No. 09/641,471, filed on Aug. 18, 2000, now Pat. No. 7,138,262.

(51) Int. Cl.
  *A61K 38/47* (2006.01)
  *C12P 21/00* (2006.01)
  *C12N 9/24* (2006.01)

(52) U.S. Cl.
  CPC ...... *C12Y 302/01045* (2013.01); *A61K 38/47* (2013.01); *C12N 9/2402* (2013.01); *C12P 21/005* (2013.01); *C12Y 302/01024* (2013.01)

(58) Field of Classification Search
  USPC .......... 435/200, 69.1, 320.1, 18; 424/94.61; 530/350; 536/23.2
  See application file for complete search history.

(56) References Cited

U.S. PATENT DOCUMENTS

| | | | |
|---|---|---|---|
| 4,925,796 A | 5/1990 | Bergh et al. | 435/97 |
| 5,236,838 A | 8/1993 | Rasmussen et al. | 435/209 |
| 5,272,066 A | 12/1993 | Bergh et al. | 435/97 |
| 5,549,892 A * | 8/1996 | Friedman et al. | 424/94.61 |
| 5,620,884 A | 4/1997 | Shorr et al. | |
| 5,641,670 A | 6/1997 | Treco et al. | |
| 5,670,132 A | 9/1997 | Griffiths et al. | |
| 5,911,983 A | 6/1999 | Barranger et al. | |
| 5,929,304 A | 7/1999 | Radin et al. | |
| 5,939,279 A * | 8/1999 | Smith et al. | 435/7.32 |
| 5,955,324 A | 9/1999 | Fan et al. | |
| 6,074,864 A | 6/2000 | Ginns et al. | |
| 6,270,989 B1 | 8/2001 | Treco et al. | 435/69.1 |
| 6,340,746 B1 | 1/2002 | Roberts et al. | |
| 6,534,300 B1 | 3/2003 | Canfield | 435/195 |
| 6,537,785 B1 | 3/2003 | Canfield | |
| 6,642,038 B1 | 11/2003 | Canfield | |
| 6,670,165 B2 | 12/2003 | Canfield | 435/195 |
| 6,770,468 B1 | 8/2004 | Canfield | |
| 6,818,233 B2 | 11/2004 | Perkes | |
| 7,138,262 B1 | 11/2006 | Daniel | |
| 7,348,000 B2 | 3/2008 | Dwek et al. | |
| 7,833,766 B2 | 11/2010 | Zhu et al. | |
| 8,673,298 B2 | 3/2014 | Zhu et al. | |
| 2002/0025550 A1 | 2/2002 | Canfield | |
| 2003/0148460 A1 | 8/2003 | Canfield | |
| 2004/0063639 A1 | 4/2004 | Gentz et al. | |
| 2004/0202666 A1 | 10/2004 | Griffiths | |
| 2004/0204379 A1 | 10/2004 | Cheng et al. | |
| 2006/0008415 A1 | 1/2006 | Kaisheva et al. | |
| 2006/0194256 A1 | 8/2006 | Miao et al. | |
| 2007/0031945 A1 | 2/2007 | Daniel | |
| 2007/0197439 A1 | 8/2007 | Zhu et al. | |
| 2007/0249689 A1 | 10/2007 | Duncan | |
| 2007/0280925 A1 | 12/2007 | Meeker et al. | |
| 2008/0003626 A1 | 1/2008 | White et al. | |
| 2008/0009516 A1 | 1/2008 | Wustman | |
| 2008/0070975 A1 | 3/2008 | Shah | |
| 2008/0081356 A1 | 4/2008 | Lasko | |
| 2011/0027254 A1 | 2/2011 | Daniel et al. | |

FOREIGN PATENT DOCUMENTS

| | | |
|---|---|---|
| CA | 2615122 | 2/2007 |
| CN | 1335505 A | 2/2002 |
| ES | 2391657 T3 | 11/2012 |
| JP | 3-503721 A | 8/1991 |

(Continued)

OTHER PUBLICATIONS

Gonzalez et al., J. Biol. Chem. 274(30):21375-21386 1999.*
Elbein, A., The FASEB Journal 5:3055-3063, 1991.*
Takahashi et al., Tohoku J. Exp. Med. 186:143-149, 1998.*
Zimran et al., The Lancet 345:451452, 1995.*
Brumshtein et al., Glycobiology 20(1):24-32, 2009.*
Van Patten et al., Glycobiology 17(5):467-478, 2007.*
Aerts et al., "Efficient Routing of Glucocerebrosidase . . . ," Biochemical and Biophysical Research Communications, 141(2):452-458, 1986.
Ahrens, "Role of Target Cell . . . ," The Journal of Biological Chemistry, 268(1):385-391, 1993.
Barton et al., "Therapeutic Response to Intravenous Infusions . . . ", Mar. 1990, Proc.Natl.Acad.Sci.USA, vol.87;1913-1916.

(Continued)

*Primary Examiner* — Delia Ramirez
(74) *Attorney, Agent, or Firm* — Troutman Sanders LLP

(57) ABSTRACT

The invention features a method of producing a high mannose glucocerebrosidase (hmGCB) which includes: providing a cell which is capable of expressing glucocerebrosidase (GCB), and allowing production of GCB having a precursor oligosaccharide under conditions which prevent the removal of at least one mannose residue distal to the pentasaccharide core of the precursor oligosaccharide of GCB, to thereby produce an hmGCB preparation. Preferably, the condition which prevents the removal of at least one mannose residue distal to the pentasaccharide core is inhibition of a class 1 processing mannosidase and/or a class 2 processing mannosidase. The invention also features an hmGCB preparation and methods of using an hmGCB preparation.

28 Claims, 1 Drawing Sheet

(56) References Cited

FOREIGN PATENT DOCUMENTS

| | | |
|---|---|---|
| JP | 07-313183 A | 12/1995 |
| JP | H10500570 A | 1/1998 |
| JP | 10-273500 A | 10/1998 |
| JP | 10-306099 A | 11/1998 |
| JP | 11-318441 A | 11/1999 |
| JP | 2003-505430 | 2/2003 |
| JP | 5364382 B2 | 12/2013 |
| JP | 5683407 B2 | 3/2015 |
| WO | 1990007573 A1 | 7/1990 |
| WO | WO 92/13067 | 8/1992 |
| WO | 9412628 A1 | 6/1994 |
| WO | WO 94/13311 | 6/1994 |
| WO | 199414837 A1 | 7/1994 |
| WO | WO 97/32591 | 9/1997 |
| WO | WO 98/02161 * | 1/1998 |
| WO | WO 98/11206 * | 3/1998 |
| WO | WO 98/22136 | 5/1998 |
| WO | 199940206 A1 | 8/1999 |
| WO | 199951724 A1 | 10/1999 |
| WO | 199957325 A2 | 11/1999 |
| WO | 199961592 A1 | 12/1999 |
| WO | 199964587 A1 | 12/1999 |
| WO | 200034490 A1 | 6/2000 |
| WO | WO 2000/76480 | 12/2000 |
| WO | WO 2001/007078 | 2/2001 |
| WO | WO 01/19955 A2 | 3/2001 |
| WO | WO 2001/19955 | 3/2001 |
| WO | 200149830 A2 | 7/2001 |
| WO | WO 2004/069190 | 8/2004 |
| WO | 2011017177 A1 | 2/2011 |
| WO | 2011107992 A | 9/2011 |
| WO | 2012012461 A2 | 1/2012 |

OTHER PUBLICATIONS

Berg-Fussman et al., "Human Acid . . . ," The Journal of Biological Chemistry, 268(20):14861-14866, 1993.

Beutler et al. (1992). Genomics, vol. 12, No. 4, pp. 795-800.

Bijsterbosch et al., "Quantitative analysis of . . . ," Eur. J. Biochem., 237:344-349, 1996.

Bischoff et al. "The effect of 1-deoxymannojirimycin on rat liver α-mannosidases" Biochem. Biophys. Res. Commun. 125(1):324-331 (1984).

Chotai et al., "The Uptake of Swainsonine . . . ," Journal of Cellular Biochemistry, 21:107-117, 1983.

Cumming, "Glycosylation of recombinant . . . ," Glycobiology, 1(2):115-130, 1991.

Daniel et al., "Effects of the . . . ," Glycoconjugate, 6:229-240, 1989.

Daniel et al., "Mammalian α-mannosidases . . . ," glycobiology, 4(5):551-566, 1994.

Elbein et al., "Kifunensine Inhibits . . . ," Archives of Biochemistry and Biophysics, 288(1):177-184, 1991.

Elbein et al., "Kifunensine, a Potent . . . ," The Journal of Biological Chemistry, 265(26):15599-15605, 1990.

Erickson et al., "Biosynthesis of the . . . ," The Journal of Biological Chemistry, 260(26)14319-14324, 1985.

Fleet et al., "Design Synthesis and . . . ," J. Chem. Soc., Chem. Commun., 1240-1241, 1984.

Friedman et al., "A Comparison of . . . ," Blood, 93:2807-2816, 1999.

Furbish et al., "Uptake and Distribution of Placental Glucocerebrosidase . . . ", 1981, Biochimica et Biophysica Acta, vol. 673; 425-434.

Marcus et al., "Glucosidase and Mannosidase . . . ," The Journal of Biological Chemistry, 275(3):1987-1992, 2000.

Martin et al., "Glycosylation and Processing of High Levels of . . . ", 1988, DNA, vol. 7, No. 2; 99-106.

Moremen et al., "Glycosidases of the . . . ," Glycobiology, 4(2):113-125, 1994.

Palamarczyk et al., "1,4-Dideoxy-1,4-imino . . . ," Archives of Biochemistry and Biophysics, 243(1):35-45, 1985.

Rudd et al., "Diversification of the . . . ," Molecular Immunology, 28(12):1369-1378, 1991.

Sato et al., "Binding, Internalization, and . . . ," J. Clin. Invest., 91:1909-1917, 1993.

Schutzbach et al. "Calcium Ion Activation of Rabbit Liver α1, 2-Mannosidase" J. Biol. Chem. 265(5):2546-2549 (1990).

Shah et al. (2003) Biochemistry, vol. 42, pp. 13812-13816.

Takasaki et al., "Structure of the . . . ," The Journal of Biological Chemistry, 259(16):10112-10117, 1984.

Tremblay et al., "Characterization of a . . . ," The Journal of Biological Chemistry, 275(41):31655-31660, 2000.

Tropea et al., "Mannostatin A, a New . . . ," Biochemistry, 29(43):10062-10069, 1990.

Tulsiani et al., "Swainsonine Inhibits . . . ," The Journal of Biological Chemistry, 257(14):7936-7939, 1982.

Weng et al., "Demonstration That a . . . ," The Journal of Biological Chemistry, 268(34):25656-25663, 1993.

Winchester et al., "The structural basis . . . ," Biochem. J., 290:743-749, 1993.

Van Weely, et al., "Function of oligosaccharide modification in glucocerebrosidase, a membrane-associated lysosomal hydrolase"., Eur. J. Biochem. 191, 669-677 (1990).

Mistry et al., "Therapeutic delivery of proteins to macrophages: implications for treatment of Gaucher's disease", The Lancet, vol. 348, No. 9041, pp. 1555-1559 (1996).

Extended European Search Report from EP Application Serial No. 10182992.7 dated Apr. 29, 2011.

Rosenberg et al., "Immunosurveillance of alglucerase enzyme therapy for Gaucher patients: Induction of humoral tolerance in seroconverted patients after repeat administration", Blood, vol. 93, pp. 2081-2088 (1999).

"Shire Human Genetic Therapies. Study of GA-GCB Enzyme Replacement Therapy in Type 1 Gaucher Disease Patients Previously Treated with Imiglucerase" Clinicaltrials.gove (2008).

Beutler et al., "Failure of Alglucerase Infused into Gaucher Disease Patients to Localize in Marrow Macrophages", Molecular Medicine, vol. 1, No. 3, pp. 320-324 (1995).

Burton et al., "Hydrophobic charge induction chromatography: salt independent protein absorption and facile elution whit aqueous buffers" Journal of Chromatography, vol. 814, pp. 71-81 (1998).

Database EMBL [online] "H.sapriens mRNA for macrophage mannose receptor" retrieved from EPI accession No. EM_STD:X55635 database accession No. X55635. Apr. 15, 1992.

Dulsat et al., "Gaucher's disease", Drugs of the Future, Prous Science, ES, vol. 34, No. 2, pp. 147-149, (2009).

Extended European Search Report from EP Application Serial No. 10806936 dated Mar. 27, 2013.

Extended European Search Report from EP Application Serial No. 11810304.3 dated Jan. 31, 2014.

Genzyme Corporation. "Cerezyme (imiglucerase) Injection, Powder, Lyophilized, for Solution." DailyMed Archived Drug Labels (online), Feb. 1, 2006, p. 1-6. Retrieved on Nov. 11, 2010.

Giraldo et al., "Safety with Velaglucerasein Two Girls Previously Treated with Imiglucerase" Spanish Gaucher Disease Foundation, P20 (presented at the 9th annual EWGGD, Cologne, Germany) (2010).

Grabowski et al., "Enzyme Thearpy in Type 1 Gaucher Disease: Comparative Efficacy of Mannose-terminated Glucocerebrosidase from Natural and Recombinant Sources", Annals of Internal Medicine, vol. 122, No. 1, pp. 33-39 (1995).

Guerrier et al., "New method for the selctive capture of antibodies under physiolgical conditions" Bioseparation, vol. 9, pp. 211-221 (2000).

International Preliminary Report on Patentability and Written Opinion from corresponding International Application Serial No. PCT/US2010/043586 dated Nov. 22, 2010.

Pastores et al. "Therapreutic Goals in the Treatement of Gaucher Disease" Seminars in Hematology 41 (suppl5):4-14. 2004.

Peterson et al., "Comparison of in vitro cellular uptake of velaglucerase alfa to that of imiclucerase" Department of Research and Development, Shire Genetic Therapies, P34 (presented at the 9th annual EWGGD, Cologne, Germany) (2010).

(56) References Cited

OTHER PUBLICATIONS

Reinke et al., "Efficacy and Tolerability of Velaglucerase Alfa in Treament of 7 patients with Type I Gaucher Disease—First Observations" Children's Hospital, Gutenberg—University of Mainz, P38 (presented at the 9th annual EWGGD, Cologne, Germany) (2010).
Richards et al. "Antibody Response in Patients with Gaucher Disease After Repeated Infusion with Macrophage-Targeted Glucocerebrosidase" Blood, 1993, vol. 82, No. 5, pp. 1402-1409.
Wadhwa et al., "Strategies for detection, measurement and characterization of unwanted antibodies induced by therapeutic biologicals" Journal of Immun. vol. 278, No. 1-2, pp. 1-17 (2003).
Wang et al. "Neutralizing antibodies to therapeutic enzymes: considerations for testing, prevention and treatment", Nature Biotechnology, vol. 26, No. 8., Aug. 1, 2008, pp. 901-908.
Wang et al., "Neutralizing antibodies to therapeutic enzymes: considerations fro testing, prevention and treatment" Nature Biotechnology, vol. 26, No. 8 pp. 901-908 (2008).
Wenhui et al., "Effectiveness of enzyme replacement therapy to patients with Gaucher Disease," China Chold Blood, 2004, vol. 9, No. 5. pp. 197-200.
Wustman et al. "Pharmacological chaperone therapy for Gaucher disease: Mechansim of action, a survey of responsive mutations and phase I clinical trial results." Molecular Genetics and Metabolism vol. 93 pp. S14-S46 (2008).
Zimran et al. "A pharmacokinetic analysis of a novel enzyme replacement therapy with Gene-Activated human glucocerebrosdiase (GA-GCB) in pateints with type I Gaucher diease." Blood Cells, Molecules, and Diseases vol. 39 pp. 115-118 (2007).
Brady et al., "Management of Neutralizing Antibody to Ceredase in a Patient With Type 3 Gaucher Disease", Pediatrics (Dec. 1997), vol. 100, No. 6, p. 1-4, http://www.pediatrics.org/cgi/content/full/100/6/e11.
Busterbosch et al., "Quantitative analysis of the targeting of mannose-terminal glucocerebrosidase Predominant uptake by liver endothelial cells", Eur. J. Biochem. (1996), vol. 237, p. 344-349.
Clinical Trial NCT00478647 Summary. <<http://clinicaltrials.gov/archive/NCT00478647/2008_08_03>>. Last accessed (Oct. 16, 2013).
Kraoua et al., "A French experience of type 3 Gaucher disease: Phenotypic diversity and neurological outcome of 10 patients", Elsevier (2011), Brain & Development 33, p. 131-139.
Tekoah et al., "Glycosylation and functionality of recombinant β-glucocerebrosidase from various production systems", Bioscience Reports (2013), p. 771-781 and Supplementary data.
Van Patten et al., "Effect of mannose chain length on targeting of glucocerebrosidase for enzyme replacement therapy of Gaucher disease", Glycobiology (2007), vol. 17, No. 5, p. 467-478.
Zang Yan et al., "14 Case report of enzyme replacement therapy to patients with Gaucher Disease" Chinese Journal of Pediatrics (2001), vol. 39, Issue 8.
Zhao et al., "Enzyme therapy of Gaucher disease: clinical and biochemical changes during production of and tolerization for neutralizing antibodies", Elsevier Science (2003), Blood Cells, Molecules, and Diseases 30, p. 90-96.
JP2014-209206 Office Action dated Oct. 27, 2015 and English Translation of Office Action, p. 1-8.
Application No. 13755466.3, European Patent Office Extended Search Report dated Oct. 20, 2015, p. 1-6.
Andersson et al. "Stabilizing effect of chemical additives against oxidation of lactate dehydrogenase" Biotechno. Appl. Biochem. 32: 145-153, (2000).
Bernier et al. "Stabilization of beta-glucosidase by polyhydric alcohols", Journal of Biotechnology 7(4):293-298, (1988).
Cleland et al. "A Specific Molar Ratio of Stabilizer to Protein is Required for Storage Stability of a Lyophilized Monoclonal Antibody", Journal of Pharmaceutical Sciences, 90(3):310-321, (2001).
European Search Report dated Oct. 29, 2014, which issued during prosecution of European Application No. 14170682.0.

Extended European Search Report dated Jul. 25, 2011, which issued during prosecution of European Application No. 10193725.8.
Furbish et al: Enzyme replacement therapy in Gaucher's disease: Large-scale purification of glucocerebrosidase suitable for human administration (hydrophobic chromatography/cholate extraction/jt-glucosidase/concanavalin A) Medical Sciences, Jan. 1, 1977 (Jan. 1, 1977), pp. 3560-3563, XP055146729, Retrieved from the Internet—URL: http://www.ncbi.nlm.nih.gov/pmc/articles/PMC431631/pdf/pnas00030-0462.pdf.
International Preliminary Report on Patentability dated Aug. 12, 2008 which issued during International Application No. PCT/US2007/061657.
International Search Report dated Jan. 3, 2002, which issued during prosecution of International Application No. PCT/US01/25882.
Kishnani et al. "A randomized trial comparing the efficacy and safety of imiglucerase (Cerezyme) infusions every 4 weeks versus every 2 weeks in the maintenance therapy of adult patients with Gaucher disease type 1." Mol Genet Metab. 96(4):164-170, (2009).
Lee et al. "The Stabilization of Proteins by Sucrose", The Journal of Biological Chemistry, 256(14):7193-7201, (1981).
Miroliaei et al. "Sugars protect native and apo yeast alcohol dehydrogenase against irreversible thermoinactivation" Enzyme and Microbial Technology, 29(8-9): 54-559, (2001).
Murray et al: "Purification of beta-glucocerebrosidase by preparative-scale high-performance liquid chromatography: The use of ethylene glycol-containing buffers for chromatography of hydrophobic glycoprotein enzymes", Analytical Biochemistry 147(2):301-310, (1985).
Nguyen et al., "Oxidation Degradation of Protein Pharmaceuticals" ACS Symp. Ser., No. 567, pp. 59-71, (1994).
Passot et al. "Physical characterisation of formulations for the development of two stable freeze-dried proteins during both dried and liquid storage" European Journal of Pharmaceutics and Biopharmaceutics, 60(3):335-348, (2005).
Starzyk et al. "The long-term international safety experience of imiglucerase therapy for Gaucher disease" Molecular Genetics and Metabolism 90:157-163, (2007).
Takahashi et al. "Enzyme therapy in Gaucher disease type 2: an autopsy case," Tohoku J. Exp. Med., 186:143-149, (1998).
Tsitsimpikou et al. "Studies of the effect of organic solvents on the stability of beta-glucosidase from Fusarium oxysporum", Biotechnology Letters 16(1):57-62 (1994).
Waldmann, "Immunotherapy: past, present and future" Nature Medicine 9:269-277, (2003).
Wang, "Lyophilization and development of solid protein pharmaceuticals" International Journal of Pharmaceutics, 203(1-2):1-60, (2000).
Written Opinion dated Aug. 21, 2008 which issued during prosecution of International Application No. PCT/US2007/061657.
Zimran et al. "Home treatment with intravenous enzyme replacement therapy for Gaucher disease: an international collaborative study of 33 patients" Blood 82(4):1107-1109, (1993).
Bembi, et al., "Enzyme Replacement Treatment in Type 1 and Type 3 Gaucher's Disease", The Lancet 344: 1679-1682 (1994).
Gornati, et al., "Total Glycolipid and Glucosylceramide Content in Serum and Urine of Patients with Gaucher's Disease Type 3 Before and After Enzyme Replacement Therapy", Clinica Chimica Acta 271(2): 151-161 (1998).
Japanese Office Action, dated Nov. 22, 2016, issued in corresponding Japanese Patent Appln. No. 2014-560086.
Sellos-Moura, et al., "Development of a Panel of Highly Sensitive, Equivalent Assays for Detection of Antibody Responses to Velaglucerase Alfa or Imiglucerase Enzyme Replacement Therapy in Patients with Gaucher Disease", Journal of Immunological Methods 373(1-2): 45-53 (2011).
Aviezer, et al., "A plant-derived recombinant human glucocerebrosidase enzyme—A Preclinical Phase I Investigation", PLoS ONE 4(3): e4792, 2009.
Fink, et al., "Correction of glucocerebrosidase deficiency after retroviral-mediated gene transfer into hematopoietic progenitor cells from patients with Gaucher disease", PNAS 87: 2334-2338, 1990.

(56) References Cited

OTHER PUBLICATIONS

"Genzyme General Clarifies Position in Gaucher's Disease Market", URL: http://biz.yahoo.com/prnews/980623/ma_genzyme_2.html, Jun. 24, 1998.
Havenga, et al., "Development of safe and efficient retroviral vectors for Gaucher disease", Gene Therapy 4: 1393-1400, 1997.
Huxtable, et al., AJP 107(1): 124-126, 1982.
Japanese Office Action, dated Feb. 9, 2016, issued in corresponding Japanese Patent Application No. 2015-045704.
Japanese Office Action, dated Sep. 20, 2016, issued in corresponding Japanese Patent Appln. No. 2014-209206.
Lee, et al., "Position of the sulfhydryl group and the disulfide bonds of human glucocerebrosidase," J. Protein Chemistry 14(3): 127-137, 1995.
Shire Limited Supplement Prospectus Investors, "Supplement to the prospectus in respect of introduction of up to 700,000,000 ordinary shares of 5 pence each to the official list", Apr. 29, 2009.
Stinchi, et al., "Targeted disruption of the lysosomal alpha-mannosidase gene results in mice resembling a mild form of human alpha-mannosidosis," Human Molecular Genetics 8(8): 1365-1372, 1999.
Sun, et al., "Saposin C is required for normal resistance of acid beta-glucosidase to proteolytic degradation," J. Biol. Chem. 278(34): 31918-31923, 2003.
Xiao, et al., "Effectiveness of enzyme replacement therapy to patients with Gaucher Disease," China Child Blood 9(5): 197-200, 2004.
Strickley RG, "Solubilizing excipients in oral and injectable formulations", Pharmaceutical Research, 21, pp. 201-230, 2004.
Jun. 21, 2017 Examiner's Report issued in connection with CA Application No. 2,768,999.
Britton DE, "Gaucher's disease: Lack of antibody response to intravenous glucocerebrosidase", Life Sci, 1978, vol. 23 No. 25, p. 2517-2519.
Jun. 22, 2017 Office Action issued in connection with Japanese Application No. 2016-136753.
Office Action dated Nov. 22, 2017 in connection with U.S. Appl. No. 14/169,628.
Weinreb N.J., "Imiglucerase and its use for the treatment of Gaucher's disease" Expert Opinion on Pharmacotherapy Aug. 2008 GB, vol. 9, No. 11, Aug. 2008, pp. 1987-2000, ISSN: 1465-6566.
EPO Office Action dated Feb. 9, 2017 in connection with EP Application No. 13755466.3.

* cited by examiner

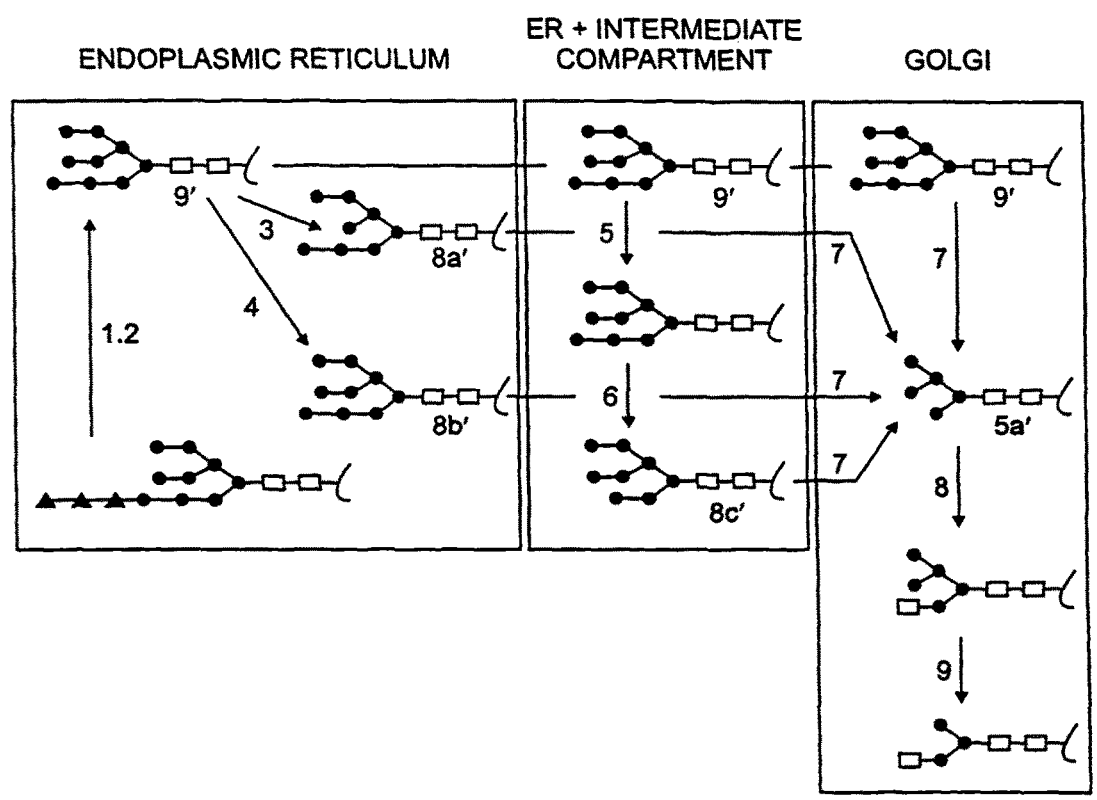

HIGH MANNOSE PROTEINS AND METHODS OF MAKING HIGH MANNOSE PROTEINS

CROSS-REFERENCE TO RELATED APPLICATION

This application is a divisional application of and claims priority to U.S. application Ser. No. 09/641,471, filed on Aug. 18, 2000, now U.S. Pat. No. 7,138,262 the contents of which are incorporated herein by reference in their entirety.

BACKGROUND OF THE INVENTION

Gaucher disease is an autosomal recessive lysosomal storage disorder characterized by a deficiency in the lysosomal enzyme, glucocerebrosidase (GCB). GCB hydrolyzes the glycolipid glucocerebroside that is formed after degradation of glycosphingolipids in the membranes of white blood cells and red blood cells. The deficiency in this enzyme causes glucocerebroside to accumulate in large quantities in the lysosomes of phagocytic cells located in the liver, spleen and bone marrow of Gaucher patients. Accumulation of these molecules causes a range of clinical manifestations including splenomegaly, hepatomegaly, skeletal disorder, thrombocytopenia and anemia. (Beutler et al. Gaucher disease; In: The Metabolic and Molecular Bases of Inherited Disease (McGraw-Hill, Inc, New York, 1995) pp. 2625-2639)

Treatments for patients suffering from this disease include administration of analgesics for relief of bone pain, blood and platelet transfusions and, in some cases, splenectomy. Joint replacement is sometimes necessary for patients who experience bone erosion.

Enzyme replacement therapy with GCB has been used as a treatment for Gaucher disease. Current treatment of patients with Gaucher disease includes administration of a carbohydrate remodeled GCB derived from human placenta or Chinese hamster ovary (CHO) cells transfected with a GCB expression construct and known as alglucerase or imiglucerase, respectively. The treatment is extremely expensive in part because of the cost of removing sugars from GCB to expose the trimannosyl core of complex glycans in order to target the enzyme to mannose receptors on cells of reticuloendothelial origin. The scarcity of the human placental tissue (in the case of alglucerase), complex purification protocols, and the relatively large amounts of the carbohydrate remodeled GCB required all contribute to the cost of the treatment.

SUMMARY OF THE INVENTION

The invention is based, in part, on the discovery that by preventing removal of one or more mannose residues distal from the pentasaccharide core of a precursor oligosaccharide chain of a protein, e.g., a lysosomal storage enzyme, a high mannose protein such as high mannose glucocerebrosidase (hmGCB) can be obtained. These high mannose proteins can be used to target the protein to cells which express mannose receptors. Such cells can include cells of reticuloendothelial origin including macrophages, Kupffer cells and histiocytes. Thus, these high mannose proteins can be used, for example, to target delivery by receptor mediated endocytosis to lysosomes to treat various lysosomal storage diseases.

In particular, hmGCB has been found to efficiently target mannose receptors. Mannose receptors are present on macrophages and other cells, e.g., dendritic cells, cardiomyocytes and glial cells, and are instrumental in receptor-mediated endocytosis. The absence of GCB in patients with Gaucher disease leads to accumulation of glucocerebroside, primarily in cells of reticuloendothelial origin including macrophages, Kupffer cells and histiocytes. Because these cells express mannose receptors on their surface, hmGCB can be used to effectively target delivery of a corrective enzyme to the lysosomes through receptor-mediated endocytosis, thereby treating Gaucher disease. Surprisingly, it was found that hmGCB uptake by macrophages was increased as compared to uptake of GCB secreted from cells.

Accordingly, in one aspect, the invention features a method of producing a preparation of high mannose glucocerebrosidase (hmGCB). The method includes:

providing a cell which is capable of expressing GCB; and allowing production of GCB having a precursor oligosaccharide under conditions which prevent the removal of at least one mannose residue distal to the pentasaccharide core of the precursor oligosaccharide of GCB, to thereby produce an hmGCB preparation.

In a preferred embodiment, the GCB is human GCB. In a preferred embodiment, the cell is a human cell.

In a preferred embodiment, the removal of: one or more α 1,2 mannose residue(s) distal to the pentasaccharide core is prevented; an α 1,3 mannose residue distal to the pentasaccharide core is prevented; and/or an α 1,6 mannose residue distal to the pentasaccharide core is prevented. Preferably, the removal of one or more α 1,2 mannose residue(s) distal to the pentasaccharide core is prevented.

In a preferred embodiment, the method can include contacting the cell with a substance which prevents the removal of at least one mannose residue distal to the pentasaccharide core of the precursor oligosaccharide of GCB, e.g., prevents removal of one or more α 1,2 mannose residue(s) distal to the pentasaccharide core, an α 1,3 mannose residue distal to the pentasaccharide core and/or an α 1,6 mannose residue distal to the pentasaccharide core. Preferably, the removal of one or more α 1,2 mannose(s) residue distal to the pentasaccharide core is prevented.

In a preferred embodiment, the method includes contacting the cell with a substance which prevents the removal of at least one mannose residue distal to the pentasaccharide core of the precursor oligosaccharide of GCB, wherein the substance is a mannosidase inhibitor. The mannosidase inhibitor can be a class 1 processing mannosidase inhibitor, a class 2 processing mannosidase inhibitor or both. The class 1 processing mannosidase inhibitor can be one or more of: kifunensine, deoxymannojirimycin, or a similar inhibitor. Preferably, the class 1 processing mannosidase inhibitor is kifunensine. Useful class 2 processing mannosidase inhibitors can include one or more of: swainsonine, mannostatin, 6-deoxy-1, 4-dideoxy-1, 4-imino-D-mannitol (6-deoxy-DIM), and 6-deoxy-6-fluoro-1, 4-dideoxy-1, 4-imino-D-mannitol (6-deoxy-6-fluoro-DIM). Preferably, the class 2 processing mannosidase inhibitor is swainsonine.

In a preferred embodiment, a mannosidase inhibitor is present at a concentration between about 0.025 to 20.0 µg/ml, 0.05 to 10 µg/ml, 0.05 to 5 µg/ml, preferably between about 0.1 to 2.0 µg/ml.

In a preferred embodiment, the method further includes contacting the cell with a class 1 processing mannosidase inhibitor and a class 2 processing mannosidase inhibitor. In a preferred embodiment, the class 1 processing mannosidase inhibitor is present at a concentration between about 0.025 to 20.0 µg/ml, 0.05 to 10 µg/ml, 0.05 to 5 µg/ml, preferably between about 0.1 to 2.0 µg/ml; the class 2 processing mannosidase inhibitor is present at a concentration between about 0.025 to 20.0 µg/ml, 0.05 to 10 µg/ml, 0.05 to 5 µg/ml, preferably between about 0.1 to 2.0 µg/ml; each of the class 1 processing and class 2 processing mannosidase inhibitors are present at a concentration between about 0.025 to 20.0 µg/ml, 0.05 to 10 µg/ml, 0.05 to 5 µg/ml, preferably between about 0.1 to 2.0 µg/ml; the total concentration of the class 1 processing and class 2 processing mannosidase inhibitors present is between about 0.025 to 40.0 µg/ml, 0.05 to 20 µg/ml, 0.05 to 10 µg/ml, preferably between about 0.1 to 4.0 µg/ml.

In a preferred embodiment, the cell carries a mutation for, e.g., a knockout for, at least one Golgi processing mannosidase. The mutation can be one which reduces the expression of the gene, reduces protein or activity levels, or alters the distribution or other post translational modifications of the mannosidase, e.g., the processing of the carbohydrate chains. The mutation can be one which reduces the level of the Golgi processing mannosidase activity, e.g., one which reduces gene expression, e.g., a null mutation, e.g., a deletion, a frameshift or an insertion. In a preferred embodiment the mutation is a knockout, e.g., in the mannosidase gene. The mutation can affect the structure (and activity of the protein), and can, e.g., be a temperature sensitive mutation or a truncation. In a preferred embodiment, the cell carries a mutation, e.g., a knockout, for: a class 1 processing mannosidase; a class 2 processing mannosidase; a class 1 processing mannosidase and a class 2 processing mannosidase. In a preferred embodiment, the class 1 processing mannosidase is: Golgi mannosidase IA; Golgi mannosidase IB; Golgi mannosidase IC; or combinations thereof. In a preferred embodiment, the class 2 processing mannosidase is: Golgi mannosidase II.

In a preferred embodiment, the cell includes a nucleic acid sequence, such as an antisense molecule or ribozyme, which can bind to or inactivate a cellular mannosidase nucleic acid sequence, e.g., mRNA, and inhibit expression of the protein. In a preferred embodiment, the nucleic acid sequence is: a class 1 processing mannosidase antisense molecule; a class 2 processing mannosidase antisense molecule; both a class 1 processing mannosidase antisense molecule and a class 2 processing mannosidase antisense molecule. In a preferred embodiment, the class 1 processing mannosidase is: Golgi mannosidase IA; Golgi mannosidase IB; Golgi mannosidase IC; and combinations thereof. In a preferred embodiment, the class 2 processing mannosidase is: Golgi mannosidase II.

In a preferred embodiment, the cell includes a molecule, e.g., an exogenously supplied molecule, which binds and inhibits a mannosidase. The molecule can be, e.g., a single chain antibody, an intracellular protein or a competitive or non-competitive inhibitor.

In a preferred embodiment, the hmGCB molecule includes a carbohydrate chain having at least four mannose residues. For example, the hmGCB molecule has at least one carbohydrate chain having five mannose residues, the hmGCB molecule has at least one carbohydrate chain having six mannose residues, the hmGCB molecule has at least one carbohydrate chain having seven mannose residues, the hmGCB molecule has at least one carbohydrate chain having eight mannose residues, the hmGCB molecule has at least one carbohydrate chain having nine mannose residues. Preferably, the hmGCB molecule has at least one carbohydrate chain having five, eight or nine mannose residues.

In a preferred embodiment, the hmGCB produced (either one or more hmGCB molecules or the preparation as a whole) has a ratio of mannose residues to GlcNAc residues which is greater than 3 mannose residues to 2 GlcNAc residues, preferably the ratio of mannose to GlcNAc is 4:2, 5:2, 6:2, 7:2, 8:2, 9:2, more preferably the ratio of mannose to GlcNAc is 5:2, 8:2 or 9:2.

In a preferred embodiment, the removal of one or more mannose residues distal to the pentasaccharide core is prevented on one, two, three or four of the carbohydrate chains of an hmGCB molecule.

In a preferred embodiment, at least 30%, 40%, 50%, 60%, 70%, 75%, 80%, 85%, 90%, 95%, 98%, 99% or all of the hmGCB molecules of the preparation have at least one, and preferably two, three or four carbohydrate chains in which the removal of one or more mannose residues distal to the pentasaccharide core has been prevented.

In a preferred embodiment, the hmGCB preparation is a relatively heterogeneous preparation. Preferably, less than 80%, 70%, 60%, 50%, 45%, 40%, 35%, 30%, 25%, 20%, 15%, 10%, 5% or 1% of the carbohydrate chains in the hmGCB preparation have the same number of mannose residues in addition to the pentasaccharide core. For example, the ratio of carbohydrate chains having the same number of mannose resides in addition to the pentasaccharide core to carbohydrate chains having a different number of mannose residues can be about: 60%:40%; 50%:50%; 40%:60%; 30%:70%; 25%:75%; 20%:80%; 15%:85%; 10%:90%; 5% or less:95% or more.

In a preferred embodiment, activity of Golgi mannosidase IA and/or IB and/or IC is inhibited and at least about 60%, 70%, 75%, 80%, 85%, 90%, 95%, 98%, 99% or 100% of the carbohydrate chains in the hmGCB preparation have five or more mannose residues, e.g., five, six, seven, eight and/or nine mannose residues. In a preferred embodiment, activity of Golgi mannosidase I is inhibited and the ratio of carbohydrate chains having five or more mannose residues to carbohydrate chains having four or less mannose residues is about 60%:40%; 70%:30%; 75%:25%; 0.80%:20%; 85%:15%; 90%:10%; 95%:5%; 99%:1%; or 100%:0%.

In a preferred embodiment, activity of Golgi mannosidase II is inhibited and at least about 60%, 70%, 75%, 80%, 85%, 90%, 95%, 98%, 99% or 100% of the carbohydrate chains in the hmGCB preparation have five or more mannose residues, e.g., five, six, seven, eight and/or nine mannose residues. In a preferred embodiment, activity of Golgi mannosidase II is inhibited and the ratio of carbohydrate chains having five or more mannose residues to carbohydrate chains having four or less mannose residues is about 60%:40%; 70%:30%; 75%:25%; 80%:20%; 85%:15%; 90%:10%; 95%:5%; 99%:1%; or 100%:0%.

In a preferred embodiment, the cell includes an exogenous nucleic acid sequence which includes a GCB coding region. In a preferred embodiment, the cell further includes a regulatory sequence, an endogenous or exogenous regulatory sequence, which functions to regulate expression of the exogenous GCB coding region.

In a preferred embodiment, the cell includes an exogenous regulatory sequence which functions to regulate expression of an endogenous GCB coding sequence, e.g., the regulatory sequence is integrated into the genome of the cell such that it regulates expression of an endogenous GCB coding sequence.

In a preferred embodiment, the regulatory sequence includes one or more of: a promoter, an enhancer, an upstream activating sequence (UAS), a scaffold-attachment region or a transcription factor-binding site. In a preferred embodiment, the regulatory sequence includes: a regulatory sequence from a metallothionein-I gene, e.g., a mouse metallothionein-I gene, a regulatory sequence from an SV-40 gene, a regulatory sequence from a cytomegalovirus gene, a regulatory sequence from a collagen gene, a regulatory sequence from an actin gene, a regulatory sequence from an immunoglobulin gene, a regulatory sequence from the HMG-CoA reductase gene, or a regulatory sequence from the EF-1α gene.

In a preferred embodiment, the cell is: a eukaryotic cell. In a preferred embodiment, the cell is of fungal, plant or animal origin, e.g., vertebrate origin. In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line. Preferably, the cell is a human cell. Examples of immortalized human cell lines useful in the present method include, but are not limited to: a Bowes Melanoma cell (ATCC Accession No. CRL 9607), a Daudi cell (ATCC Accession No. CCL 213), a HeLa cell and a derivative of a HeLa cell (ATCC Accession Nos. CCL2 CCL2.1 and CCL 2.2), a HL-60 cell (ATCC Accession No. CCL 240), an HT-1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Raji cell (ATCC Accession No. CCL 86), a RPMI 8226 cell (ATCC Accession No. CCL 155), a U-937 cell (ATCC Accession No. 1593), WI-28VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927-5932, 1988), as well as heterohybridoma cells produced by fusion of human cells and cells of another species. In another embodiment, the immortalized cell line can be cell line other than a human cell line, e.g., a CHO cell line, a COS cell line. In another embodiment, the cell can be a from a clonal cell strain or clonal cell line.

In a preferred embodiment, a population of cells which are capable of expressing hmGCB is provided, and at least 30%, 40%, 50%, 60%, 70%, 75%, 80%, 85%, 90%, 95%, 98%, 99% or all of the cells produce hmGCB molecules with at least one carbohydrate chain, and preferably two, three, or four carbohydrate chains, having the specified number of mannose residues.

In a preferred embodiment, the cell is cultured in culture medium which includes at least one mannosidase inhibitor. In a preferred embodiment, the method further includes obtaining the hmGCB from the medium in which the cell is cultured.

In another aspect, the invention features a method of producing a preparation of hmGCB. The method includes:
providing a cell which is capable of expressing GCB; and
allowing production of GCB having a precursor oligosaccharide under conditions which inhibit class 1 processing mannosidase activity and class 2 processing mannosidase activity such that the removal of at least one mannose residue distal to the pentasaccharide core of the precursor oligosaccharide of GCB is prevented, to thereby produce an hmGCB preparation.

In a preferred embodiment, the GCB is human GCB. In a preferred embodiment, the cell is a human cell.

In a preferred embodiment, the removal of: one or more α 1,2 mannose residue(s) distal to the pentasaccharide core is prevented; an α 1,3 mannose residue distal to the pentasaccharide core is prevented; and/or an α 1,6 mannose residue distal to the pentasaccharide core is prevented. Preferably, the removal of one or more α 1,2 mannose residue(s) distal to the pentasaccharide core is prevented.

In a preferred embodiment, the method can include: contacting the cell with a substance which inhibits a class 1 processing mannosidase activity and a substance which inhibits a class 2 processing mannosidase activity thereby preventing the removal of at least one mannose residue distal to the pentasaccharide core of the precursor oligosaccharide of GCB. In a preferred embodiment, the substances prevent removal of one or more α 1,2 mannose residue distal to the pentasaccharide core.

In a preferred embodiment, the method includes contacting the cell with a substance which inhibits a class 1 processing mannosidase activity and a substance which inhibits a class 2 processing mannosidase activity, wherein the substances are a class 1 processing mannosidase inhibitor and a class 2 processing mannosidase inhibitor. In a preferred embodiment, the class 1 processing mannosidase inhibitor can be one or more of: kifunensine, deoxymannojirimycin, or a similar inhibitor. Preferably, the class 1 processing mannosidase inhibitor is kifunensine. In a preferred embodiment, the class 2 processing mannosidase inhibitor can be one or more of: swainsonine, mannostatin, 6-deoxy-DIM, and 6-deoxy-6-fluoro-DIM. Preferably, the class 2 processing mannosidase inhibitor is swainsonine.

In a preferred embodiment, a class 1 processing mannosidase inhibitor is present at a concentration between about 0.025 to 20.0 µg/ml, 0.05 to 10 µg/ml, 0.05 to 5 µg/ml, preferably between about 0.1 to 2.0 µg/ml; a class 2 processing mannosidase inhibitor is present at a concentration between about 0.025 to 20.0 µg/ml, 0.05 to 10 µg/ml, 0.05 to 5 µg/ml, preferably between about 0.1 to 2.0 µg/ml; each of the class 1 processing and class 2 processing mannosidase inhibitors are present at a concentration between about 0.025 to 20.0 µg/ml, 0.05 to 10 µg/ml, 0.05 to 5 µg/ml, preferably between about 0.1 to 2.0 µg/ml; the total concentration of the class 1 processing and class 2 processing mannosidase inhibitors present is between about 0.025 to 40.0 µg/ml, 0.05 to 20 µg/ml, 0.05 to 10 µg/ml, preferably between is about 0.1 to 4.0 µg/ml.

In a preferred embodiment, the cell carries a mutation for, e.g., a knockout for, a class 1 mannosidase and a class 2 mannosidase. The mutation can be one which reduces the expression of the gene, reduces protein or activity levels, or alters the distribution or other post translational modifications of the mannosidase, e.g., the processing of the carbohydrate chains. The mutation can be one which reduces the level of a class 1 processing mannosidase and/or a class 2 processing mannosidase activity, e.g., one which reduces gene expression, e.g., a null mutation, e.g., a deletion, a frameshift, or an insertion. In a preferred embodiment, the mutation is a knockout in the mannosidase gene. The mutation can affect the structure (and activity of the protein), and can, e.g., be a temperature sensitive mutant. In a preferred embodiment, the class 1 processing mannosidase is: Golgi mannosidase IA; Golgi mannosidase IB; Golgi mannosidase IC; combinations thereof. In a preferred embodiment, the class 2 processing mannosidase is: Golgi mannosidase II.

In a preferred embodiment, the cell includes both a class 1 processing mannosidase antisense molecule and a class 2 processing mannosidase antisense molecule. In a preferred embodiment, the class 1 processing mannosidase is: Golgi mannosidase IA; Golgi mannosidase IB; Golgi mannosidase IC; combinations thereof. In a preferred embodiment, the class 2 processing mannosidase is: Golgi mannosidase II.

In a preferred embodiment, the cell includes a molecule, e.g., an exogenously supplied molecule, which binds and inhibits a mannosidase. The molecule can be, e.g., a single chain antibody, an intracellular protein or a competitive or non-competitive inhibitor.

In a preferred embodiment, the class 1 processing mannosidase activity and the class 2 mannosidase activity can be inhibited by different mechanisms. For example, a class 1 processing mannosidase activity can be inhibited by contacting the cell with a substrate which inhibits a class 1 processing mannosidase, e.g., a class 1 mannosidase inhibitor, and the class 2 processing mannosidase can be inhibited by using a cell which is a knockout of a class 2 mannosidase and/or includes a class 2 mannosidase antisense molecule. In another preferred embodiment, a class 2 processing mannosidase activity can be inhibited by contacting the cell with a substrate which inhibits a class 2 processing mannosidase, e.g., a class 2 mannosidase inhibitor, and the class 1 processing mannosidase can be inhibited by using a cell which is a knockout of a class 1 mannosidase and/or includes a class 1 mannosidase antisense molecule.

In a preferred embodiment, the hmGCB molecule includes a carbohydrate chain having at least four mannose residues. For example, the hmGCB molecule has at least one carbohydrate chain having five mannose residues, the hmGCB molecule has at least one carbohydrate chain having six mannose residues, the hmGCB molecule has at least one carbohydrate chain having seven mannose residues, the hmGCB molecule has at least one carbohydrate chain having eight mannose residues, the hmGCB molecule has at least one carbohydrate chain having nine mannose residues. Preferably, the hmGCB molecule has at least one carbohydrate chain having five, eight or nine mannose residues.

In a preferred embodiment, the hmGCB produced (either one or more hmGCB molecules or the preparation as a whole) has a ratio of mannose residues to GlcNAc residues which is greater than 3 mannose residues to 2 GlcNAc residues, preferably the ratio of mannose to GlcNAc is 4:2, 5:2, 6:2, 7:2, 8:2, 9:2, more preferably the ratio of mannose to GlcNAc is 8:2 or 9:2.

In a preferred embodiment, the removal of one or more mannose residues distal to the pentasaccharide core is prevented on one, two, three or four of the carbohydrate chains of the hmGCB molecule.

In a preferred embodiment, at least 30%, 40%, 50%, 60%, 70%, 75%, 80%, 85%, 90%, 95%, 98%, 99% or all of the hmGCB molecules of the preparation have at least one, and preferably two, three or four carbohydrate chains in which the removal of one or more mannose residues distal to the pentasaccharide core has been prevented.

In a preferred embodiment, the hmGCB preparation is a relatively heterogeneous preparation. Preferably, less than 80%, 70%, 60%, 50%, 45%, 40%, 35%, 30%, 25%, 20%, 15%, 10%, 5% or 1% of the carbohydrate chains in the hmGCB preparation have the same number of mannose residues in addition to the pentasaccharide core. For example, the ratio of carbohydrate chains having the same number of mannose resides in addition to the pentasaccharide core to carbohydrate chains having a different number of mannose residues can be about: 60%:40%; 50%:50%; 40%:60%; 30%:70%; 25%:75%; 20%:80%; 15%:85%; 10%:90%; 5% or less:95% or more.

In a preferred embodiment, activity of a class 1 processing mannosidase, e.g., Golgi mannosidase IA and/or Golgi mannosidase IB and/or Golgi mannosidase IC, and activity of a class 2 processing mannosidase, e.g., Golgi mannosidase II, are inhibited and at least about 60%, 70%, 75%, 80%, 85%, 90%, 95%, 98%, 99% or 100% of the carbohydrate chains in the hmGCB preparation have five or more mannose residues, e.g., five, six, seven, eight and/or nine mannose residues. In a preferred embodiment, activity of a class 1 processing mannosidase, e.g., Golgi mannosidase IA and/or Golgi mannosidase IB and/or Golgi mannosidase IC, and activity of a class 2 processing mannosidase, e.g., Golgi mannosidase II, are inhibited and the ratio of carbohydrate chains having five or more mannose residues to carbohydrate chains having four or less mannose residues, respectively, is about 60%:40%; 70%:30%; 75%:25%; 80%:20%; 85%:15%; 90%:10%; 95%:5%; 99%:1%; or 100%:0%.

In a preferred embodiment, the cell includes an exogenous nucleic acid sequence which includes a GCB coding region. In a preferred embodiment, the cell further includes a regulatory sequence, an endogenous or exogenous regulatory sequence, which functions to regulate expression of the exogenous GCB coding region.

In a preferred embodiment, the cell includes an exogenous regulatory sequence which functions to regulate expression of an endogenous GCB coding sequence, e.g., the regulatory sequence is integrated into the genome of the cell such that it regulates expression of an endogenous GCB coding sequence.

In a preferred embodiment, the regulatory sequence includes one or more of: a promoter, an enhancer, an upstream activating sequence (UAS), a scaffold-attachment region or a transcription factor-binding site. In a preferred embodiment, the regulatory sequence includes: a regulatory sequence from a metallothionein-I gene, e.g., a mouse metallothionein-I gene, a regulatory sequence from an SV-40 gene, a regulatory sequence from a cytomegalovirus gene, a regulatory sequence from a collagen gene, a regulatory sequence from an actin gene, a regulatory sequence from an immunoglobulin gene, a regulatory sequence from the HMG-CoA reductase gene, or a regulatory sequence from the EF-1α gene.

In a preferred embodiment, the cell is: a eukaryotic cell. In a preferred embodiment, the cell is of fungal, plant or animal origin, e.g., vertebrate origin. In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line. Preferably, the cell is a human cell. Examples of immortalized human cell lines useful in the present method include, but are not limited to: a Bowes Melanoma cell (ATCC Accession No. CRL 9607), a Daudi cell (ATCC Accession No. CCL 213), a HeLa cell and a derivative of a HeLa cell (ATCC Accession Nos. CCL2 CCL2.1 and CCL 2.2), a HL-60 cell (ATCC Accession No. CCL 240), an HT-1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Raji cell (ATCC Accession No. CCL 86), a RPMI 8226 cell (ATCC Accession No. CCL 155), a U-937 cell (ATCC Accession No. 1593), WI-28VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927-5932, 1988), as well as heterohybridoma cells produced by fusion of human cells and cells of another species. In another embodiment, the immortalized cell line can be cell line other than a human cell line, e.g., a CHO cell line, a COS cell line. In another embodiment, the cell can be from a clonal cell strain or clonal cell line.

In a preferred embodiment, a population of cells which are capable of expressing hmGCB is provided, and at least 30%, 40%, 50%, 60%, 70%, 75%, 80%, 85%, 90%, 95%, 98%, 99% or all of the cells produce hmGCB with at least one carbohydrate chain, preferably two, three, or four carbohydrate chains, having the specified number of mannose residues.

In a preferred embodiment, the cell is cultured in a culture medium which includes at least one class 1 processing mannosidase inhibitor and at least one class 2 processing mannosidase inhibitor. In a preferred embodiment, the method further includes obtaining the hmGCB from the medium in which the cell is cultured.

In another aspect, the invention features a method of producing a preparation of hmGCB. The method includes:
providing a cell into which a nucleic acid sequence comprising an exogenous regulatory sequence has been introduced such that the regulatory sequence regulates the expression of an endogenous GCB coding region; and
allowing production of GCB having a precursor oligosaccharide under conditions which prevent the removal of at least one mannose residue distal to the pentasaccharide core of the precursor oligosaccharide of GCB, to thereby produce an hmGCB preparation.

In a preferred embodiment, the GCB is human GCB.

In a preferred embodiment, the removal of: one or more α 1,2 mannose residue(s) distal to the pentasaccharide core is prevented; an α 1,3 mannose residue distal to the pentasaccharide core is prevented; and/or an α 1,6 mannose residue distal to the pentasaccharide core is prevented. Preferably, the removal of one or more α 1,2 mannose residue(s) distal to the pentasaccharide core is prevented.

In a preferred embodiment, the method can include contacting the cell with a substance which prevents the removal of at least one mannose residue distal to the pentasaccharide core of the precursor oligosaccharide of GCB, e.g., prevents removal of one or more α 1,2 mannose residue(s) distal to the pentasaccharide core, an α 1,3 mannose residue distal to the pentasaccharide core and/or an α 1,6 mannose residue distal to the pentasaccharide core. Preferably, the removal of one or more α 1,2 mannose(s) residue distal to the pentasaccharide core is prevented.

In a preferred embodiment, the method includes contacting the cell with a substance which prevents the removal of at least one mannose residue distal to the pentasaccharide core of the precursor oligosaccharide of GCB, and the substance is a mannosidase inhibitor. The mannosidase inhibitor can be a class 1 processing mannosidase inhibitor, a class 2 processing mannosidase inhibitor or both. The class 1 processing mannosidase inhibitor can be one or more of: kifunensine, deoxymannojirimycin, or a similar inhibitor. Preferably, the class 1 processing mannosidase inhibitor is kifunensine. Useful class 2 processing mannosidase inhibitors can include one or more of: swainsonine, mannostatin, 6-deoxy-DIM, 6-deoxy-6-fluoro-DIM. Preferably, the class 2 processing mannosidase inhibitor is swainsonine.

In a preferred embodiment, a mannosidase inhibitor is present at a concentration between about 0.025 to 20.0 µg/ml, 0.05 to 10 µg/ml, 0.05 to 5 µg/ml, preferably between about 0.1 to 2.0 µg/ml.

In a preferred embodiment, the method further includes contacting the cell with a class 1 processing mannosidase inhibitor and a class 2 processing mannosidase inhibitor. In a preferred embodiment, a class 1 processing mannosidase inhibitor is present at a concentration between about 0.025 to 20.0 µg/ml, 0.05 to 10 µg/ml, 0.05 to 5 µg/ml, preferably between about 0.1 to 2.0 µg/ml; a class 2 processing mannosidase inhibitor is present at a concentration between about 0.025 to 20.0 µg/ml, 0.05 to 10 µg/ml, 0.05 to 5 µg/ml, preferably between about 0.1 to 2.0 µg/ml; each of the class 1 processing and class 2 processing mannosidase inhibitors are present at a concentration between about 0.025 to 20.0 gig/ml, 0.05 to 10 µg/ml, 0.05 to 5 µg/ml, preferably between about 0.1 to 2.0 µg/ml; the total concentration of the class 1 processing and class 2 processing mannosidase inhibitors present is between about 0.025 to 40.0 µg/ml, 0.05 to 20 µg/ml, 0.05 to 10 g/ml, preferably between about 0.1 to 4.0 µg/ml.

In a preferred embodiment, the cell carries a mutation for, e.g., a knockout for, at least one mannosidase. The mutation can be one which reduces the expression the gene, reduces protein or activity levels, or alters the distribution or other post translational modifications of the mannosidase, e.g., the processing of the carbohydrate chains. The mutation can be one which reduces the level of the Golgi processing mannosidase activity, e.g., one which reduces gene expression, e.g., a null mutation, e.g., a deletion, a frameshift or an insertion. In a preferred embodiment the mutation is a knockout, e.g., in the mannosidase gene. The mutation can affect the structure (and activity of the protein), and can, e.g., be a temperature sensitive mutation or a truncation. In a preferred embodiment, the cell carries a mutation, e.g., a knockout, for: a class 1 processing mannosidase; a class 2 processing mannosidase; a mutant, e.g., a knockout, for a class 1 processing mannosidase and a class 2 processing mannosidase. In a preferred embodiment, the class 1 processing mannosidase is: Golgi mannosidase IA; Golgi mannosidase IB; Golgi mannosidase IC; or combinations thereof. In a preferred embodiment, the class 2 processing mannosidase is: Golgi mannosidase II.

In a preferred embodiment, the cell includes a nucleic acid sequence, such as an antisense molecule or ribozyme, which can bind to or inactivate a cellular mannosidase nucleic acid sequence, e.g., mRNA, and inhibit expression of the protein. In a preferred embodiment, the nucleic acid sequence is: a class 1 processing mannosidase antisense molecule; a class 2 processing mannosidase antisense molecule; both a class 1 processing mannosidase antisense molecule and a class 2 processing mannosidase antisense molecule. In a preferred embodiment, the class 1 processing mannosidase is: Golgi mannosidase IA; Golgi mannosidase IB; Golgi mannosidase IC; combinations thereof. In a preferred embodiment, the class 2 processing mannosidase is: Golgi mannosidase II.

In a preferred embodiment, the cell includes a molecule, e.g., an exogenously supplied molecule, which binds and inhibits a mannosidase. The molecule can be, e.g., a single chain antibody, an intracellular protein or a competitive or non-competitive inhibitor.

In a preferred embodiment, the hmGCB molecule includes a carbohydrate chain having at least four mannose residues. For example, the hmGCB molecule has at least one carbohydrate chain having five mannose residues, the hmGCB molecule has at least one carbohydrate chain having six mannose residues, the hmGCB molecule has at least one carbohydrate chain having seven mannose residues, the hmGCB molecule has at least one carbohydrate chain having eight mannose residues, the hmGCB molecule has at least one carbohydrate chain having nine mannose residues. Preferably, the hmGCB molecule has at least one carbohydrate chain having five, eight or nine mannose residues.

In a preferred embodiment, the hmGCB produced (either one or more hmGCB molecules or the preparation as a whole) has a ratio of mannose residues to GlcNAc residues which is greater than 3 mannose residues to 2 GlcNAc residues, preferably the ratio of mannose to GlcNAc is 4:2, 5:2, 6:2, 7:2, 8:2, 9:2, more preferably the ratio of mannose to GlcNAc is 5:2, 8:2 or 9:2.

In a preferred embodiment, the removal of one or more mannose residues distal to the pentasaccharide core is prevented on one, two, three or four of the carbohydrate chains of the hmGCB molecule.

In a preferred embodiment, at least 30%, 40%, 50%, 60%, 70%, 75%, 80%, 85%, 90%, 95%, 98%, 99% or all of the hmGCB molecules of the preparation have at least one, and preferably two, three or four carbohydrate chains in which the removal of one or more mannose residues distal to the pentasaccharide core has been prevented.

In a preferred embodiment, the hmGCB preparation is a relatively heterogeneous preparation. Preferably, less than 80%, 70%, 60%, 50%, 45%, 40%, 35%, 30%, 25%, 20%, 15%, 10%, 5% or 1% of the carbohydrate chains in the hmGCB preparation have the same number of mannose residues in addition to the pentasaccharide core. For example, the ratio of carbohydrate chains having the same number of mannose resides in addition to the pentasaccharide core to carbohydrate chains having a different number of mannose residues can be about: 60%:40%; 50%:50%; 40%:60%; 30%:70%; 25%:75%; 20%:80%; 15%:85%; 10%:90%; 5% or less:95% or more.

In a preferred embodiment, activity of Golgi mannosidase IA and/or IB and/or IC is inhibited and at least about 60%, 70%, 75%, 80%, 85%, 90%, 95%, 98%, 99% or 100% of the carbohydrate chains in the hmGCB preparation have five or more mannose residues, e.g., five, six, seven, eight, and/or nine mannose residues. In a preferred embodiment, activity of Golgi mannosidase I is inhibited and the ratio of carbohydrate chains having five or more mannose residues to carbohydrate chains having four or less mannose residues is about 60%:40%; 70%:30%; 75%:25%; 80%:20%; 85%:15%; 90%:10%; 95%:5%; 99%:1%; or 100%:0%.

In a preferred embodiment, activity of Golgi mannosidase II is inhibited and at least about 60%, 70%, 75%, 80%, 85%, 90%, 95%, 98%, 99% or 100% of the carbohydrate chains in the hmGCB preparation have five or more mannose residues. In a preferred embodiment, activity of Golgi mannosidase II is inhibited and the ratio of carbohydrate chains having five or more mannose residues to carbohydrate chains having four or less mannose residues is about 60%:40%; 70%:30%; 75%:25%; 80%:20%; 85%:15%; 90%:10%; 95%:5%; 99%:1%; or 100%:0%.

In a preferred embodiment, the regulatory sequence includes one or more of: a promoter, an enhancer, an upstream activating sequence (UAS), a scaffold-attachment region or a transcription factor-binding site. In a preferred embodiment, the regulatory sequence includes: a regulatory sequence from a metallothionein-I gene, e.g., a mouse metallothionein-I gene, a regulatory sequence from an SV-40 gene, a regulatory sequence from a cytomegalovirus gene, a regulatory sequence from a collagen gene, a regulatory sequence from an actin gene, a regulatory sequence from an immunoglobulin gene, a regulatory sequence from the HMG-CoA reductase gene, or a regulatory sequence from the EF-la gene.

In a preferred embodiment, the cell is: a eukaryotic cell. In a preferred embodiment, the cell is of fungal, plant or animal origin, e.g., vertebrate origin. In a preferred embodiment, the cell is: mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line. Preferably, the cell is a human cell. Examples of immortalized human cell lines useful in the present method include, but are not limited to: a Bowes Melanoma cell (ATCC Accession No. CRL 9607), a Daudi cell (ATCC Accession No. CCL 213), a HeLa cell and a derivative of a HeLa cell (ATCC Accession Nos. CCL2, CCL2.1 and CCL 2.2), a HL-60 cell (ATCC Accession No. CCL 240), an HT-1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Raji cell (ATCC Accession No. CCL 86), a RPMI 8226 cell (ATCC Accession No. CCL 155), a U-937 cell (ATCC Accession No. 1593), WI-28VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927-5932, 1988), as well as heterohybridoma cells produced by fusion of human cells and cells of another species. In another embodiment, the immortalized cell line can be cell line other than a human cell line, e.g., a CHO cell line, a COS cell line. In another embodiment, the cell can be from a clonal cell strain or clonal cell line.

In a preferred embodiment, a population of cells which are capable of expressing hmGCB is provided, and at least 30%, 40%, 50%, 60%, 70%, 75%, 80%, 85%, 90%, 95%, 98%, 99% or all of the cells produce hmGCB with at least one carbohydrate chain, preferably two, three, or four carbohydrate chains, having the specified number of mannose residues.

In a preferred embodiment, the cell is cultured in culture medium which includes at least one mannosidase inhibitor. In a preferred embodiment, the method further includes obtaining the hmGCB from the medium in which the cell is cultured.

In another aspect, the invention features an hmGCB molecule, e.g., an hmGCB molecule described herein, e.g., a human hmGCB, produced by any of the methods described herein. Preferably, the hmGCB molecule includes at least one carbohydrate chain, preferably two, three, or four carbohydrate chains, having at least four mannose residues of a precursor oligosaccharide chain.

In another aspect, the invention features an hmGCB preparation which includes a portion of hmGCB molecules which include at least one carbohydrate chain, preferably two, three, or four carbohydrate chains, having at least four mannose residues of a precursor oligosaccharide chain. Preferably, the hmGCB preparation is produced by any of the methods described herein.

In a preferred embodiment, the hmGCB is human hmGCB.

In a preferred embodiment, the hmGCB molecule can have: at least one carbohydrate chain having five mannose residues; at least one carbohydrate chain having six mannose residues; at least one carbohydrate chain having seven mannose residues; at least one carbohydrate chain having eight mannose residues; at least one carbohydrate chain having nine mannose residues.

In a preferred embodiment, the hmGCB produced (either one or more hmGCB molecules or the preparation as a whole) has at least one carbohydrate chain having a ratio of mannose residues to GlcNAc residues which is greater than 3 mannose residues to 2 GlcNAc residues, preferably the ratio of mannose to GlcNAc is 4:2, 5:2, 6:2, 7:2, 8:2, 9:2, more preferably the ratio of mannose to GlcNAc is 5:2, 8:2 or 9:2.

In a preferred embodiment, at least 30%, 40%, 50%, 60%, 70%, 75%, 80%, 85%, 90%, 95%, 98%, 99% or all of the hmGCB of the preparation have at least one, preferably, two, three or four carbohydrate chains in which the removal of one or more mannose residues distal to the pentasaccharide core has been prevented.

In another aspect, the invention features a cell having at least one mannosidase activity inhibited and which includes a nucleic acid sequence comprising an exogenous regulatory sequence which has been introduced such that the regulatory sequence regulates the expression of an endogenous GCB coding region, wherein the cell produces GCB in which the removal of at least one mannose residue distal to the pentasaccharide core of a precursor oligosaccharide of GCB is prevented.

In a preferred embodiment, the cell produces an hmGCB preparation, e.g., a human hmGCB preparation, in which the removal of: one or more α 1,2 mannose residue(s) distal to the pentasaccharide core is prevented; an α 1,3 mannose residue distal to the pentasaccharide core is prevented; and/or an α 1,6 mannose residue distal to the pentasaccharide core is prevented. Preferably, the removal of one or more α 1,2 mannose residue(s) distal to the pentasaccharide core is prevented.

In a preferred embodiment, at least one mannosidase activity in the cell has been inhibited by contacting the cell with a substance which inhibits a mannosidase. In a preferred embodiment, the substance is a mannosidase inhibitor. The mannosidase inhibitor can be a class 1 processing mannosidase inhibitor, a class 2 processing mannosidase inhibitor or both. In a preferred embodiment, the class 1 processing mannosidase inhibitor can be one or more of: kifunensine and deoxymannojirimycin. Preferably, the class 1 processing mannosidase inhibitor is kifunensine. In a preferred embodiment, the class 2 processing mannosidase inhibitor can be one or more of: swainsonine, mannostatin, 6-deoxy-DIM, and 6-deoxy-6-fluoro-DIM. Preferably, the class 2 processing mannosidase inhibitor is swainsonine.

In a preferred embodiment, the cell carries a mutation for, e.g., a knockout for, at least one Golgi processing mannosidase. The mutation can be one which reduces the expression of the gene, reduces protein or activity levels, or alters the distribution or other post translational modifications of the mannosidase, e.g., the processing of a carbohydrate chain. The mutant can be one which reduces the level of Golgi processing mannosidase activity, e.g., one which reduces gene expression, e.g., a null mutation, e.g., a deletion, a frameshift, or an insertion. In a preferred embodiment, the mutation is a knockout in the mannosidase gene. The mutation can affect the structure (and activity of the protein), and can, e.g., be a temperature sensitive mutation. In a preferred embodiment, the cell is a mutant, e.g., a knockout, for: a class 1 processing mannosidase; a class 2 processing mannosidase; a class 1 processing mannosidase and a class 2 processing mannosidase. In a preferred embodiment, the class 1 processing mannosidase is: Golgi mannosidase IA; Golgi mannosidase IB; Golgi mannosidase IC; combinations thereof. In a preferred embodiment, the class 2 processing mannosidase is: Golgi mannosidase II.

In a preferred embodiment, the cell further includes a nucleic acid sequence, such as an antisense molecule or ribozyme, which can bind to or inactivate a cellular mannosidase nucleic acid sequence, e.g., mRNA, and inhibit expression of the protein. In a preferred embodiment, the nucleic acid sequence is: a class 1 processing mannosidase antisense molecule; a class 2 processing mannosidase antisense molecule; both a class 1 processing mannosidase antisense molecule and a class 2 processing mannosidase antisense molecule. In a preferred embodiment, the class 1 processing mannosidase is: Golgi mannosidase IA; Golgi mannosidase IB; Golgi mannosidase IC; combinations thereof. In a preferred embodiment, the class 2 processing mannosidase is: Golgi mannosidase II.

In a preferred embodiment, the cell includes a molecule, e.g., an exogenously supplied molecule, which binds and inhibits a mannosidase. The molecule can be, e.g., a single chain antibody, an intracellular protein or a competitive or non-competitive inhibitor.

In a preferred embodiment, the hmGCB molecule produced by the cell has a ratio of mannose residues to GlcNAc residues which is greater than 3 mannose residues to 2 GlcNAc residues, preferably the ratio of mannose to GlcNAc is 4:2, 5:2, 6:2, 7:2, 8:2, 9:2, more preferably the ratio of mannose to GlcNAc is 5:2, 8:2 or 9:2.

In a preferred embodiment, the cell is unable to remove of one or more mannose residues distal to the pentasaccharide core on one, two, three or four of the carbohydrate chains of hmGCB.

In a preferred embodiment, at least 30%, 40%, 50%, 60%, 70%, 75%, 80%, 85%, 90%, 95%, 98%, 99% or all of the hmGCB molecules produced by the cell have at least one, preferably, two, three or four carbohydrate chains in which the removal of one or more mannose residues distal to the pentasaccharide core has been prevented.

In a preferred embodiment, the regulatory sequence includes one or more of: a promoter, an enhancer, an upstream activating sequence (UAS), a scaffold-attachment region or a transcription factor-binding site. In a preferred embodiment, the regulatory sequence includes: a regulatory sequence from a metallothionein-I gene, e.g., a mouse metallothionein-I gene, a regulatory sequence from an SV-40 gene, a regulatory sequence from a cytomegalovirus gene, a regulatory sequence from a collagen gene, a regulatory sequence from an actin gene, a regulatory sequence from an immunoglobulin gene, a regulatory sequence from the HMG-CoA reductase gene, or a regulatory sequence from the EF-la gene.

In a preferred embodiment, the cell is: a eukaryotic cell. In a preferred embodiment, the cell is of fungal, plant or animal origin, e.g., vertebrate origin. In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line. Preferably, the cell is a human cell. Examples of immortalized human cell lines useful in the present method include, but are not limited to: a Bowes Melanoma cell (ATCC Accession No. CRL 9607), a Daudi cell (ATCC Accession No. CCL 213), a HeLa cell and a derivative of a HeLa cell (ATCC Accession Nos. CCL2, CCL2.1, and CCL 2.2), a HL-60 cell (ATCC Accession No.

CCL 240), an HT-1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Raji cell (ATCC Accession No. CCL 86), a RPMI 8226 cell (ATCC Accession No. CCL 155), a U-937 cell (ATCC Accession No. 1593), WI-28VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927-5932, 1988), as well as heterohybridoma cells produced by fusion of human cells and cells of another species. In another embodiment, the immortalized cell line can be cell line other than a human cell line, e.g., a CHO cell line, a COS cell line. In another embodiment, the cell can be from a clonal cell strain or clonal cell line.

In another aspect, the invention features a pharmaceutical composition-which includes an hmGCB molecule, e.g., a human hmGCB, which includes at least one carbohydrate chain, preferably two, three, or four carbohydrate chains, having at least four mannose residues of a precursor oligosaccharide chain, in an amount suitable for treating Gaucher disease.

In a preferred embodiment, the pharmaceutical composition further includes a pharmaceutically acceptable carrier or diluent.

Another aspect of the invention features a method of treating a subject having Gaucher disease. The method includes administering to a subject having Gaucher disease an hmGCB preparation, e.g., a human hmGCB preparation, which includes at least one carbohydrate chain, preferably two, three, or four carbohydrate chains, having at least four mannose residues of a precursor oligosaccharide chain, in an amount suitable for treating Gaucher disease.

In another aspect, the invention features a method of purifying hmGCB from a sample. The method includes: providing a harvested hmGCB product; and subjecting the hmGCB product to hydrophobic charge induction chromatography (HCIC) and/or hydrophobic interaction chromatography (HIC), thereby obtaining purified hmGCB.

In a preferred embodiment, MEP Hypercel® is used for HCIC. In another preferred embodiment, MacroPrep Methyl® is used for HIC.

In another preferred embodiment, the method further includes subjecting the hmGCB product to ion exchange chromatography. The hmGCB product can be subjected to HCIC and/or HIC prior to ion exchange chromatography or the hmGCB product can be subjected to ion exchange chromatography prior to HCIC and/or HIC. Preferably, the hmGCB product is subjected to more than one ion exchange chromatography step. The ion exchange chromatography can be: anion exchange chromatography, cation exchange chromatography or both.

In a preferred embodiment, anion exchange chromatography is performed using one or more of: Q Sepharose Fast Flow®, MacroPrep High Q Support®, DEAE Sepharose Fast Flow®, and Macro-Prep DEAE®. In a preferred embodiment, cation exchange chromatography is performed using one or more of: SP Sepharose Fast Flow®, Source 30S®, CM Sepharose Fast Flow®, Macro-Prep CM Support®, and Macro-Prep High S Support®.

In a preferred embodiment, the method further includes subjecting the hmGCB product to size exclusion chromatography. Preferably, the size exclusion chromatography is performed using one or more of: Superdex 200®, Sephacryl S-200 HR® and Bio-Gel A 1.5M®.

In another aspect, the invention features a method of purifying hmGCB. The method includes: providing a harvested hmGCB product; subjecting the hmGCB product to hydrophobic charge induction chromatography (HCIC) and/or hydrophobic interaction chromatography (HIC); and subjecting the hmGCB product to one or more of anion exchange chromatography, cation exchange chromatography, and size exclusion chromatography, to thereby obtain purified hmGCB.

In a preferred embodiment, MEP Hypercel® is used for HCIC. In another preferred embodiment, MacroPrep Methyl® is used for HIC.

In a preferred embodiment, the method includes using anion exchange chromatography. Preferably, anion exchange chromatography is performed using one or more of: Q Sepharose Fast Flow®, MacroPrep High Q Support®, DEAE Sepharose Fast Flow®, and Macro-Prep DEAE®.

In a preferred embodiment, the method includes using cation exchange chromatography. Preferably, cation exchange chromatography is performed using one or more of: SP Sepharose Fast Flow®, Source 30S®, CM Sepharose Fast Flow®, Macro-Prep CM Support®, and Macro-Prep High S Support®.

In a preferred embodiment, the method includes using size exclusion chromatography. Preferably, the size exclusion chromatography is performed using one or more of: Superdex 200®, Sephacryl S-200 HR® and Bio-Gel A 1.5M®.

In a preferred embodiment, the hmGCB is subjected to (in any order): anion exchange chromatography and cation exchange chromatography; anion exchange chromatography and size exclusion chromatography; cation exchange chromatography and size exclusion chromatography; anion exchange chromatography, cation exchange chromatography and size exclusion chromatography. Preferably, the hmGCB is subjected to all three of these chromatography steps in the following order: anion exchange chromatography, cation exchange chromatography and size exclusion chromatography.

In another aspect, the invention features a method of purifying hmGCB. The method includes: providing a harvested hmGCB product; subjecting the hmGCB product to hydrophobic charge induction chromatography (HCIC) and/or hydrophobic interaction chromatography (HIC); subjecting the HCIC and/or HIC purified hmGCB product to anion exchange chromatography; subjecting the anion exchange purified hmGCB to cation exchange chromatography; and, subjecting the cation exchange purified hmGCB to size exclusion chromatography, to thereby obtain purified hmGCB.

In a preferred embodiment, MEP Hypercel® is used for HCIC. In another preferred embodiment, MacroPrep Methyl® is used for HIC.

In a preferred embodiment, anion exchange chromatography is performed using one or more of: Q Sepharose Fast Flow®, MacroPrep High Q Support®, DEAE Sepharose Fast Flow®, and Macro-Prep DEAE®.

In a preferred embodiment, cation exchange chromatography is performed using one or more of: SP Sepharose Fast Flow®, Source 30S®, CM Sepharose Fast Flow®, Macro-Prep CM Support®; and Macro-Prep High S Support®.

In a preferred embodiment, size exclusion chromatography is performed using one or more of: Superdex 200®, Sephacryl S-200 HR® and Bio-Gel A 1.5M®.

The term "high mannose glucocerebrosidase (hmGCB)" as used herein refers to glucocerebrosidase having at least one carbohydrate chain having four or more mannose residues from a precursor oligosaccharide. Preferably, the hmGCB has five, six, seven, eight or nine mannose residues from the precursor oligosaccharide chain. Most preferably, the hmGCB has five, eight or nine mannose residues from the precursor oligosaccharide chain.

The term "hmGCB preparation" refers to two or more hmGCB molecules.

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. A "clonal cell strain" is defined as a cell strain that is derived from a single founder cell. A "heterogenous cell strain" is defined as a cell strain that is derived from two or more founder cells.

"Immortalized cells", as used herein, are cell lines (as opposed to cell strains with the designation "strain" reserved for primary and secondary cells), a critical feature of which is that they exhibit an apparently unlimited lifespan in culture.

The term "transfected cell" refers to a cell into which an exogenous synthetic nucleic acid sequence, e.g., a sequence which encodes a protein, is introduced. Once in the cell, the synthetic nucleic acid sequence can integrate into the recipients cells chromosomal DNA or can exist episomally. Standard transfection methods can be used to introduce the synthetic nucleic acid sequence into a cell, e.g., transfection mediated by liposome, polybrene, DEAE dextran-mediated transfection, electroporation, calcium phosphate precipitation or microinjection. The term "transfection" does not include delivery of DNA or RNA into a cell by a virus The term "infected cell" or "transduced cell" refers to a cell into which an exogenous synthetic nucleic acid sequence, e.g., a sequence which encodes a protein, is introduced by a virus. Viruses known to be useful for gene transfer include an adenovirus, an adeno-associated virus, a herpes virus, a mumps virus, a poliovirus, a retrovirus, a Sindbis virus, a lentivirus and a vaccinia virus such as a canary pox virus.

Other features and advantages of the invention will be apparent from the following detailed description, and from the claims.

BRIEF DESCRIPTION OF THE DRAWING

FIG. 1 is a diagram showing the trimming of N-linked glycans as it occurs in the endoplasmic reticulum, the intermediate compartment and in the Golgi apparatus. The enzymes are numbered as follows: (1) α-glucosidase I; (2) α-glucosidase II; (3) ER mannosidase I; (4) ER mannosidase II; (5) ER glucosyl transferase; (6) endomannosidase; (7) Golgi mannosidase IA, IB and IC; (8) GlcNAc transferase I; (9) Golgi mannosidase II. ▲, Glucose; □, GlcNAc; ●, Mannose. Enzymes (3) and (7) are inhibited by kifunensine; enzyme (9) is inhibited by swainsonine.

DETAILED DESCRIPTION OF THE INVENTION

The invention is based, in part, on the discovery that inhibition of the removal of one or more mannose residues distal from the pentasaccharide core of a precursor oligosaccharide chain of glucocerebrosidase (GCB), results in high mannose glucocerebrosidase (hmGCB) that is efficiently targeted to mannose receptors. The removal of a mannose residue from the pentasaccharide core of a precursor oligosaccharide chain can be prevented by inhibiting or reducing the activity of one or more mannosidase enzymes, e.g., one or more class 1 processing mannosidase(s) and/or class 2 processing mannosidase(s). By preventing or inhibiting the removal of one or more mannose residues, hmGCB having at least one carbohydrate chain with four or more mannose residues from the precursor oligosaccharide chain can be obtained.

Gaucher disease is caused by a deficiency of GCB. GCB is required for degradation of glycosphingolipid glucocerebroside. In the absence of GCB, the glucocerebroside accumulates primarily in phagocytic cells, e.g., macrophages, and, ultimately, builds up in the liver, spleen and bone marrow.

Macrophages have mannose receptors. These receptors play a role in receptor-mediated endocytosis by these cells. hmGCB efficiently targets the mannose receptors on macrophages and improves the uptake of GCB (in the form of hmGCB) into these cells. By directing GCB (in the form of hmGCB) to the cells in which glucocerebroside accumulates, hmGCB can be used to hydrolyze glucocerebroside in the macrophages, thereby reducing the subsequent accumulation of this glycolipid in the liver, spleen and bone marrow of patients having Gaucher disease.

Glucocerebrosidase

Nucleotide sequence information is available for genes encoding glucocerebrosidase from various species. (See Horowitz et al. (1989) *Genomics* 4(1):87-96; Beutler et al. (1992) *Genomics* 12(4):795-800).

Mature human GCB has five potential N-linked glycosylation sites at Asn-19, Asn-59, Asn-146, Asn-270, and Asn-462. Glycosylation occurs at four of the five sites in human tissue derived GCB (Erickson et al. (1985) *J. Biol. Chem.* 260:14319-14324). Studies employing site-directed mutagenesis have demonstrated that the site at Asn-462 is never occupied (Berg-Fussman et al. (1993) J. Biol. Chem. 268: 14861-14866). Approximately 20% of the released glycan chains from human placental GCB were shown to be of the high mannose type containing up to seven mannose residues, whereas the majority of the glycan chains were of the complex type with sialylated biantennary and triantennary structures. (Takasaki et al. (1984) *J. Biol. Chem.* 259:10112-10117)

The first event in GCB N-glycosylation is the co-translational transfer in the lumen of the endoplasmic reticulum (ER) of $Glc_3Man_9GlcNAc_2$ from oligosaccharide-PP-dolichol to nascent peptide. The presence of the three glucose residues on the donor oligosaccharide allows for efficient transfer to an acceptor asparagine by oligosaccharyl transferase. Following N-glycosylation, the glucose residues are rapidly removed from GCB during the folding process by ER glucosidases I and II. Two different ER mannosidases are each capable of hydrolyzing a single mannose residue from Man$_9$GlcNAc$_2$ to form two different isomers of Man$_8$GlcNAc$_2$ (see FIG. 1). Accessible glycans are then further processed in the Golgi to Man$_5$GlcNAc$_2$ by the removal of up to four α1,2-linked mannose residues by Golgi mannosidase I. There are at least three different human genes encoding related Golgi mannosidase I isoforms (IA, IB, and IC) with slightly different substrate specificities and tissue expression but all are capable of trimming four mannose residues from Man$_9$GlcNAc$_2$ glycans to form Man$_5$GlcNAc$_2$ (Tremblay et al. (Jul. 27, 2000) *J. Biol. Chem.* [epub ahead of print]). They are located on chromosomes 6q22, 1p13, and 1p35-36 and their cDNA sequences are obtainable from GenBank as X74837, AF027156, and AF261655, respectively.

The final stage of processing that commits a glycan to the biosynthetic pathway for complex glycans requires the initial conversion of Man$_5$GlcNAc$_2$ to GlcNAcMan$_5$GlcNAc$_2$ by the action of GlcNAc transferase I, after which Golgi mannosidase II can catalyse the removal of two further mannose residues to yield GlcNAcMan$_3$GlcNAc$_2$. This is the substrate for glycan elongation by glycosyl transferases located in the trans Golgi and the trans Golgi network to form complex type chains.

If the high mannose chains transferred to GCB in the initial N-glycosylation step can be prevented from being processed to complex chains in the Golgi, then GCB with high mannose chains (hmGCB) will effectively target the mannose receptors on reticuloendothelial cells.

Cells

Primary and secondary cells to be transfected or infected can be obtained from a variety of tissues and include cell types which can be maintained and propagated in culture. For example, primary and secondary cells which can be transfected or infected include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Primary cells are preferably obtained from the individual to whom the transfected or infected primary or secondary cells are administered (i.e., an autologous cell). However, primary cells may be obtained from a donor (other than the recipient) of the same species (i.e., an allogeneic cell) or another species (i.e., a xenogeneic cell) (e.g., mouse, rat, rabbit, cat, dog, pig, cow, bird, sheep, goat, horse, monkey, baboon).

Primary or secondary cells of vertebrate, particularly mammalian, origin can be transfected or infected with an exogenous DNA sequence, e.g., an exogenous DNA sequence encoding a therapeutic protein, and produce an encoded therapeutic protein stably and reproducibly, both in vitro and in vivo, over extended periods of time. In addition, the transfected or infected primary and secondary cells can express the encoded product in vivo at physiologically relevant levels, cells can be recovered after implantation and, upon reculturing, to grow and display their preimplantation properties. Cells can be modified to reduce cell surface histo compatibility complex or foreign carbohydrate moieties to reduce immunogenecity, e.g., a universal donor cell.

Alternatively, primary or secondary cells of vertebrate, particularly mammalian, origin can be transfected or infected with an exogenous DNA sequence which includes a regulatory sequence. Examples of such regulatory sequences include one or more of: a promoter, an enhancer, an UAS, a scaffold attachment region or a transcription binding site. The targeting event can result in the insertion of the regulatory sequence of the DNA sequence, placing a targeted endogenous gene under their control (for example, by insertion of either a promoter or an enhancer, or both, upstream of the endogenous gene or regulatory region). Optionally, the targeting event can simultaneously result in the deletion of an endogenous regulatory sequence, such as the deletion of a tissue-specific negative regulatory sequence, of a gene. The targeting event can replace an existing regulatory sequence; for example, a tissue-specific enhancer can be replaced by an enhancer that has broader or different cell-type specificity than the endogenous elements, or displays a pattern of regulation or induction that is different from the corresponding nontransfected or noninfected cell. In this regard, the endogenous sequences are deleted and new sequences are added. Alternatively, the endogenous regulatory sequences are not removed or replaced but are disrupted or disabled by the targeting event, such as by targeting the exogenous sequences within the endogenous regulatory elements. Introduction of a regulatory sequence by homologous recombination can result in primary or secondary cells expressing a therapeutic protein which it does not normally express. In addition, targeted introduction of a regulatory sequence can be used for cells which make or contain the therapeutic protein but in lower quantities than normal (in quantities less than the physiologically normal lower level) or in defective form, and for cells which make the therapeutic protein at physiologically normal levels, but are to be augmented or enhanced in their content or production. Methods of activating an endogenous coding sequence are described in U.S. Pat. No. 5,641,670, U.S. Pat. No. 5,733,761 and U.S. Pat. No. 5,968,502, the contents of which are incorporated herein by reference.

The transfected or infected primary or secondary cells may also include a DNA sequence encoding a selectable marker which confers a selectable phenotype upon them, facilitating their identification and isolation. Methods for producing transfected primary or secondary cells which stably express the DNA sequence, clonal cell strains and heterogenous cell strains of such transfected cells, methods of producing the clonal and heterogenous cell strains, are known and described, for example, in U.S. Pat. No. 5,641, 670, U.S. Pat. No. 5,733,761 and U.S. Pat. No. 5,968,502, the contents of which are incorporated herein by reference.

Transfected primary or secondary cells, can be made by electroporation. Electroporation is carried out at appropriate voltage and capacitance (and corresponding time constant) to result in entry of the DNA construct(s) into the primary or secondary cells. Electroporation can be carried out over a wide range of voltages (e.g., 50 to 2000 volts) and corresponding capacitance. Total DNA of approximately 0.1 to 500 μg is generally used.

Alternatively, known methods such as calcium phosphate precipitation, microinjection, modified calcium phosphate precipitation and polybrene precipitation, liposome fusion and receptor-mediated gene delivery can be used to transfect cells.

Processing of Glucocerebrosidase

Oligosaccharide assembly in cells which have not been treated to prevent removal of mannose residues usually proceeds as discussed below: The oligosaccharide chains of GCB are attached to the polypeptide backbone by N-glycosidic linkages. N-linked glycans have an amide bond that connects the anomeric carbon (C-1) of a reducing-terminal N-acetylglucosamine (GlcNAc) residue of the oligosaccharide and a nitrogen of an asparagine (Asn) residue of the polypeptide.

Initiation of N-linked oligosaccharide assembly does not occur directly on the Asn residues of the GCB protein, but rather involves preassembly of a lipid-linked 14 sugar precursor oligosaccharide which is then transferred to the protein in the ER during or very soon after its translation from mRNA. A "precursor oligosaccharide" as used herein refers to the oligosaccharide chain involved in the initial steps in biosynthesis of carbohydrate chains. A "precursor oligosaccharide" can be an oligosaccharide structure which includes at least the following sugars: $Man_9GlcNAc_2$, for example, a precursor oligosaccharide can have the following structure: $Glc_3Man_9GlcNAc_2$, as shown in FIG. 1. The precursor oligosaccharide is synthesized while attached via a pyrophosphate bridge to a polyisoprenoid carrier lipid, a dolichol. This assembly involves at least six distinct membrane-bound glycosyltransferases. Some of these enzymes transfer monosaccharides from nucleotide sugars, while others utilize dolichol-linked monosaccharides as sugar donors. After assembly of the lipid-linked precursor is complete, another membrane-bound enzyme transfers it to sterically accessible Asn residues which occur as part of the sequence -Asn-X-Ser/Thr-.

Glycosylated Asn residues of newly-synthesized GCB transiently carry $Glc_3Man_9GlcNAc_2$, also referred to herein as an "unprocessed carbohydrate chain".

The processing of N-linked oligosaccharides is accomplished by the sequential action of a number of membrane-bound enzymes and begins immediately after transfer of the precursor oligosaccharide $Glc_3Man_9GlcNAc_2$ to the protein. The terms "processing", "trimming" and "modifying" are used interchangeably herein.

N-linked oligosaccharide processing can be divided into three stages: removal of the three glucose residues, removal of a variable number of mannose residues, and addition of various sugar residues to the resulting trimmed core.

The removal of the glucose residues in the first stage of processing involves removal of all three glucose residues to generate N-linked $Man_9GlcNAc_2$. This structure is also referred to herein as: Manα1-2Manα1-2Manα1-3[Manα1-2Manα1-3(Manα1-2Manα1-6)Manα1-6]Manβ1-4GlcNAcβ1-4GlcNAc (See FIG. 1, structure 9'). Processing normally continues to the second stage with removal of mannose residues.

Four of the mannose residues of the $Man_9GlcNAc_2$ moiety are bound by α 1,2 linkages. Up to four of these α 1,2-linked mannose residues can be removed by mannosidase IA, IB and IC to generate N-linked $Man_{5-8}GlcNAc_2$.

Protein-linked $Man_5GlcNAc_2$ can then serve as a substrate for GlcNAc transferase I, which transfers a β 1,2-linked GlcNAc residue from UDP-GlcNAc to the core α 1,3-linked mannose residue to form $GlcNAcMan_5GlcNAc_2$. Mannosidase II can then complete the trimming phase of the processing pathway by removing two mannose residues to generate a protein-linked oligosaccharide which contains within it a $Man_3GlcNAc_2$, the "pentasaccharide core". The structure $GlcNAcMan_3GlcNAc_2$ is then a substrate for Glc-NAc transferase II, which can transfer a β 1,2-linked Glc-NAc residue to the α 1,6-linked mannose residue.

After the trimming phase, monosaccharides are sequentially added to the growing oligosaccharide chain by a series of membrane-bound Golgi glycosyltransferases, each of which is highly specific with respect to the acceptor oligosaccharide, the donor sugar, and the type of linkage formed between the sugars. These can include distinct GlcNAc transferases (producing β 1,2; β 1, 4; or β 1,6 linkages); galactosyltransferases (producing β 1, 4; β 1,3; and α 1,3 linkages); sialyltransferases (one producing α 2, 3 and another, α 2, 6 linkages); fucosyltransferases (producing α 1,2; α 1,3; α 1, 4 or α 1,6 linkages); and a growing list of other enzymes responsible for a variety of unusual linkages. The cooperative action of these glycosyltransferases produces a diverse family of structures collectively referred to as "complex" oligosaccharides. These may contain two, three or four outer branches ("antennae") attached to the invariant core pentasaccharide, $Man_3GlcNAc_2$. These structures are referred to in terms of the number of their outer branches: biantennary (two branches), triantennary (three branches) or tetraantennary (four branches). The size of these complex glycans can vary.

Processing of High Mannose Glucocerebrosidase hmGCB can be produced by reducing or preventing cellular carbohydrate modification (i.e., processing) of GCB. Carbohydrate modification can be prevented by allowing production of GCB under conditions which prevent the removal of at least one mannose residue distal to the pentasaccharide core of a precursor oligosaccharide chain of GCB. For example, one or more of the "trimming" stages during the removal of mannose residues from a precursor oligosaccharide can be prevented.

Cellular mannosidases fall into two broad classes: class 1 processing enzymes, which include ER mannosidase I, Golgi mannosidase IA, IB and IC and which hydrolyze α1,2-linked mannose residues, and require $Ca^{2+}$ for activity; and class 2 processing enzymes, which include ER mannosidase II, Golgi mannosidase II, cytosolic α-mannosidase, and lysosomal α-mannosidase and which have a broader substrate specificity and do not require $Ca^{2+}$ for activity.

The trimming of mannose residues from the precursor oligosaccharide involves at least the following mannosidase enzymes: Golgi mannosidase IA, IB and IC, and Golgi mannosidase II. By inhibiting one or more of these mannosidases during N-linked oligosaccharide assembly in a cell, GCB can be produced which has at least one carbohydrate chain with one or more mannose residues in addition to the pentasaccharide core. For example, inhibition of both ER mannosidase I and Golgi mannosidase I can produce hmGCB with at least one carbohydrate chain (and preferably all chains) having at least eight mannose residues from the precursor oligosaccharide; inhibition of Golgi mannosidase II can produce hmGCB with at least one carbohydrate chain (and preferably all chains) having at least five mannose residues from the precursor oligosaccharide.

Trimming by a mannosidase can be inhibited, for example, by contacting the cell with a substance which prevents the removal of one or more mannose residues from a precursor oligosaccharide of GCB or by producing GCB in a cell which does not produce or produces at deficient levels at least one mannosidase, or in a cell which produces a mutated and/or inactive mannosidase. For example, the cell can be a knockout for at least one mannosidase, can express at least one antisense mannosidase molecule or can be dominant negative for at least one mannosidase.

Substances which Prevent Removal of Mannose Residues

A substance which prevents the removal of one or more mannose residues from a precursor oligosaccharide of GCB can be used to produce an hmGCB preparation. For example, a cell which expresses GCB can be contacted with a substance which prevents the removal of one or more α 1,2 mannose residues of a precursor oligosaccharide of GCB, and/or removal of an α 1,3 mannose residue of a precursor oligosaccharide of GCB, and/or removal of an α 1,6 mannose residue of a precursor oligosaccharide of GCB. Preferably, the substance is a mannosidase inhibitor, e.g., a class 1 processing mannosidase inhibitor or a class 2 processing mannosidase inhibitor.

Cellular mannosidases fall into two broad classes on the basis of protein sequence homologies (Moremen et al. (1994) *Glycobiology* 4:113-125). These two classes are mechanistically different. Class 1 enzymes, which include ER mannosidase I and Golgi mannosidase I isoforms, have a mass of about 63-73 kDa, hydrolyze α1,2-linked mannose residues and require $Ca^{2+}$ for activity. Class 1 processing mannosidases can be blocked, for example, by treatment with a substrate mimic, e.g., a pyranose analog of mannose. For example, class 1 processing mannosidases can be blocked by treatment with one or more of the following enzymatic inhibitors: kifunensine, deoxymannojirimycin, or a combination thereof. Class 2 enzymes, which include ER mannosidase I, Golgi mannosidase II, cystolic α-mannosidase, and lysosomal α-mannosidase, have a greater mass of about 107-136 kDa, do not require $Ca^{2+}$ for activity and have a broader substrate specificity. Class 2 processing mannosidases can be blocked, for example, by treatment with furanose transition state analogues of the mannosyl cation (Daniels et al. (1994) *Glyco Biol.* 4:551-566). For example, class 2 processing mannosidases can by blocked by treatment with one or more of the following inhibitors: swainsonine, 6-deoxy-DIM, 6-deoxy-6-fluoro-DIM, mannostatin A, or combinations thereof.

Kifunensine can be used as an inhibitor of the endoplasmic reticulum mannosidase I and/or Golgi mannosidase IA and/or IB and/or IC; deoxymannojirimycin can be used as an inhibitor of ER mannosidase I, ER mannosidase II and/or of Golgi mannosidase IA and/or IB and/or IC; swainsonine can be used an inhibitor of Golgi mannosidase II; and mannostatin A can be used as an inhibitor of Golgi mannosidase II.

Use of a mannosidase inhibitor can inhibit the processing of a carbohydrate chain of GCB past a certain stage of mannose residue trimming during oligosaccharide assembly. For example, contacting a cell with kifunensine can inhibit trimming of any, or one, two, three, or four of the mannose residues of a precursor oligosaccharide.

Processing α-mannosidases can be blocked by treatment of cells with one or more of the following enzyme inhibitors:

Kifunensine, an inhibitor of the endoplasmic reticulum I and Golgi mannosidase I enzymes (Weng and Spiro (1993) *J. Biol. Chem* 268:25656-25663; Elbein et al. (1990) *J. Biol. Chem* 265:15599-15605).

Swainsonine, an inhibitor of the Golgi mannosidase II enzyme (Tulsiani et al. (1982) *J. Biol. Chem* 257:7936-7939).

Deoxymannojirimycin, an inhibitor of both endoplasmic reticulum mannosidases I and II and of Golgi mannosidase I (Weng and Spiro (1993) *J. Biol. Chem* 268: 25656-25663; Tremblay and Herscovics (2000) J. Biol. Chem. July 27; [epub ahead of print])

DIM (1,4-dideoxy-1,4-imino-D-mannitol), an inhibitor of Golgi mannosidase II (Palamarzyk et al. (1985) *Arch. Biochem. Biophys.* 243:35-45).

6-Deoxy-DIM and 6-deoxy-6-fluoro-DIM, inhibitors of Golgi mannosidase II (Winchester et al. (1993) *Biochem J.* 290:743-749).

A, an inhibitor of Golgi mannosidase II (Tropea et al. (1990) *Biochemistry* 29:10062-10069).

Various mannosidase inhibitors can be selected by their ability to penetrate particular cell types as well as by the inhibitory potency of the mannosidase inhibitor. For example, swainsonine is rapidly internalized by cultured fibroblasts in a time- and concentration-dependent manner. Swainsonine is also a potent inhibitor of a class 2 mannosidase, e.g., Golgi mannosidase II. Thus, swainsonine can be used to produce hmGCB in cultured fibroblasts, e.g., hmGCB having at least one carbohydrate chain which has at least four or five mannose residues of the precursor oligosaccharide. In addition, kifunensine is readily taken up by cultured fibroblasts and is a potent inhibitor of class 1 mannosidases, e.g., ER mannosidase I and Golgi mannosidase I. Thus, kifunensine can be used to produce hmGCB in cultured fibroblasts, e.g., hmGCB having at least one carbohydrate chain which has at least four, five, six, seven, eight or nine mannose residues of the precursor oligosaccharide.

Preferably, the mannosidase inhibitor is present at a concentration of 0.025 to 20.0 µg/ml, 0.05 to 10 µg/ml, 0.05 to 5 µg/ml, preferably between about 0.1 to 2.0 µg/ml. For example, a class 1 processing mannosidase inhibitor can be present at a concentration between about 0.025 to 20.0 µg/ml, 0.05 to 10 µg/ml, 0.05 to 5 µg/ml, preferably between about 0.1 to 2.0 µg/ml; a class 2 processing mannosidase inhibitor can be present at a concentration between about 0.025 to 20.0 µg/ml, 0.05 to 10 µg/ml, 0.05 to 5 µg/ml, preferably between about 0.1 to 2.0 µg/ml; each of the class 1 processing and class 2 processing mannosidase inhibitors can be present at a concentration between about 0.025 to 20.0 µg/ml, 0.05 to 10 µg/ml, 0.05 to 5 µg/ml, preferably between about 0.1 to 2.0 µg/ml; or the total concentration of the class 1 processing and class 2 processing mannosidase inhibitors present can be between about 0.025 to 40.0 µg/ml, 0.05 to 20 µg/ml, 0.05 to 10 µg/ml, preferably between about 0.1 to 5.0 µg/ml.

The cell can be contacted with a mannosidase inhibitor by, for example, culturing the cell on medium which includes at least one mannosidase inhibitor.

Mannosidase Mutant Cell

Mannosidase Knockout Cell

Permanent or regulated inactivation of mannosidase gene expression can be achieved by targeting to a mannosidase locus with a transfected plasmid DNA construct or a synthetic oligonucleotide. The plasmid construct or oligonucleotide can be designed to several forms. These include the following: 1) insertion of selectable marker genes or other sequences within an exon of a mannosidase gene; 2) insertion of exogenous sequences in regulatory regions of non-coding sequence; 3) deletion or replacement of regulatory and/or coding sequences; and, 4) alteration of a protein coding sequence by site specific mutagenesis.

In the case of insertion of a selectable marker gene into coding sequence, it is possible to create an in-frame fusion of an endogenous mannosidase exon with the mannosidase exon engineered to contain, for example, a selectable marker gene. In this way following successful targeting, the endogenous mannosidase gene expresses a fusion mRNA (mannosidase sequence plus selectable marker sequence). Moreover, the fusion mRNA would be unable to produce a functional mannosidase translation product.

In the case of insertion of DNA sequences into regulatory regions, the transcription of a mannosidase gene can be silenced by disrupting the endogenous promoter region or any other regions in the 5' untranslated region (5' UTR) that is needed for transcription. Such regions include, for example, translational control regions and splice donors of introns. Secondly, a new regulatory sequence can be inserted upstream of the mannosidase gene that would render the mannosidase gene subject to the control of extracellular factors. It would thus be possible to down-regulate or extinguish mannosidase gene expression as desired for optimal hmGCB production. Moreover, a sequence which includes a selectable marker and a promoter can be used to disrupt expression of the endogenous sequence. Finally, all or part of the endogenous mannosidase gene could be deleted by appropriate design of targeting substrates.

In order to create a cell which includes a knockout of at least one chromosomal copy of the human Golgi mannosidase IA, IB or IC gene, the genomic DNA comprising at least the 5' portion of the gene (including regulatory sequences, 5' UTR, coding sequence) is isolated. For example, the GenBank sequence, Accession No.: NM005907 (human), can be used to generate a probe for Golgi mannosidase IA or Accession Nos.: AAF97058 can be used to generate a probe for Golgi mannosidase IB or IC using polymerase chain reaction (PCR). Oligonucleotides for PCR can be designated based upon the GenBank sequence. The resulting probe can hybridize to the single copy Golgi mannosidase IA, IB or IC gene. This probe can then be used to screen a commercially available recombinant phage library (e.g., a library made from human genomic DNA) to isolate a clone comprising all or part of the mannosidase I structural genes. Once a recombinant clone comprising a mannosidase regulatory and/or coding sequence is isolated, specific targeting plasmids designed to achieve the inactivation of mannosidase gene expression can then be constructed. Inactivation of mannosidase activity results from the insertion of exogenous DNA into regulatory or coding sequences to disrupt the translational reading frame. Inactivation of the enzyme can also be the result of disruption of mRNA transcription or mRNA processing, or by deletion of endogenous mannosidase regulatory or coding sequences.

The nucleic acid sequence of other class 1 and class 2 processing mannosidase are also available, for example, in GenBank. Using the methods described above for Golgi mannosidase IA, IB or IC, a knockout cell for other class 1 and/or class 2 processing mannosidases can be produced.

A mannosidase knockout cell can be used, for example, in gene therapy. A knockout cell can be administered to a subject, e.g., a subject having Gaucher disease, such that the cell produces hmGCB in vivo.

Antisense Mannosidase Nucleic Acid Sequences

Nucleic acid molecules which are antisense to a nucleotide encoding a mannosidase, e.g., a class I processing or class 2 processing mannosidase, can be used as an inactivating agent which inhibits expression of a mannosidase. For example, Golgi mannosidase IA, Golgi mannosidase IB, Golgi mannosidase IC, and/or Golgi mannosidase II expression can be inhibited by an antisense nucleic acid molecule. An "antisense" nucleic acid includes a nucleotide sequence which is complementary to a "sense" nucleic acid encoding a mannosidase, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire mannosidase coding strand, or to only a portion thereof. For example, an antisense nucleic acid molecule which antisense to the "coding region" of the coding strand of a nucleotide sequence encoding a mannosidase can be used.

As the coding strand sequences encoding various mannosidases are disclosed in, for example, Bause (1993) *Eur. J. Biochem.* 217(2):535-540; Gonzalez et al. (1999) *J. Biol. Chem.* 274(30):21375-21386; Misago et al. (1995) *Proc. Natl Acad. Sci. USA* 92(25):11766-11770; Tremblay et al. (1998) *Glycobiology* 8(6):585-595, Tremblay et al. (2000) *J. Biol. Chem. July* 27:[epub ahead of print], antisense nucleic acids can be designed according to the rules of Watson and Crick base pairing. The antisense nucleic acid molecule can comprise sequence complementary to the entire coding region of a mannosidase mRNA, but more preferably is an oligonucleotide which is complementary to only a portion of the coding or noncoding region of a mannosidase mRNA. For example, the antisense oligonucleotide can comprise sequence complementary to the region surrounding the translation start site of a mannosidase mRNA. An antisense oligonucleotide can be, for example, about 5, 10, 15, 20, 25, 30, 35, 40, 45, 50, or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation relative to a target nucleic acid of interest.

Purification of hmGCB

The term "purified" hmGCB, as used herein, refers to hmGCB that is substantially free of cellular material when produced by a cell which expresses GCB. The language "substantially free of cellular material" includes preparations of hmGCB in which the protein is separated from cellular components of the cells in which it is produced. In one embodiment, the language "substantially free of cellular material" includes preparations of hmGCB having less than about 30% (by dry weight) of non-GCB protein (also referred to herein as a "protein impurity" or "contaminating protein"), more preferably less than about 20% of non-GCB protein, still more preferably less than about 10% of non-GCB protein, and most preferably less than about 5% non-GCB protein. When the hmGCB is obtained (i.e., harvested) from culture media, it is also preferably substantially free of a component of the culture medium, i.e., components of the culture medium represent less than about 20%, more preferably less than about 10%, and most preferably less than about 5% of the dry weight of the protein preparation.

Various methods can be used to harvest hmGCB from culture media. The term "harvested hmGCB" as used herein refers to hmGCB obtained from culture media or from a cell. For example, one of the following alternatives can be used to prepare the harvested hmGCB prior to a purification procedure. These can include: 1) filtering the fresh harvest; 2) filtering the fresh harvest and freezing, e.g., at about −20° C. to −80° C., the filtered product until ready for processing (at which time it can be thawed and, optionally, filtered); 3) filtering the fresh harvest, concentrating filtered product (e.g., by about 8 to 10 fold), and then, optionally, filtering again; 4) filtering the fresh harvest, concentrating filtered product (e.g., by about 8 to 10 fold), optionally, filtering again, and then freezing, e.g., at about −20° C. to −80° C., until ready for processing (at which time it can be thawed and, optionally, filtered). Variations of these alternatives can also be performed. For example, when the harvested product or concentrated harvested product is frozen, different harvests can be pooled after thawing and filtered. In addition, for harvested or concentrated harvested product, the product can be held at a cooling temperature, e.g., about 2° C. to 8° C., for short periods of time, e.g., about 1 to 3 days, preferably 1 day, prior to purification. The harvested product held at the cooling temperature can be pooled prior to purification.

When a concentration of harvest is performed, an ultrafiltration membrane with a 5,000 to 50,000 mw cutoff, preferably a 10,000 to 30,000 mw cutoff, can be employed. Filter clarification will typically employ a 1.2 μm/0.5 μm prefilter, followed by a 0.2 μm final filter.

HmGCB can be purified by the following purification techniques. For example, hydrophobic charge induction chromatography (HCIC) can be used to purify the hmGCB preparation. Alternatively, hydrophobic interaction chromatography (HIC) can be used to purify the hmGCB preparation. Both HCIC and HIC are described below.

HCIC or HIC can be used alone or in combination with one or more ion exchange steps. Ion exchange steps that can be used in combination with an HCIC or HIC step (either before or after HCIC or HIC) include the use of anion exchange and/or cation exchange chromatography. Generally known commercially available anion exchange supports used in the purification of proteins bear quaternary ammonium functional groups. Preferred matrices for use in the present process are agarose or cellulose based matrices such as microcrystalline cellulose or cross-linked agaroses. Also particularly preferred are those matrices bearing diethyl aminoethyl, triethyl aminomethyl, or trimethyl aminomethyl functional groups. A particularly preferred anion exchange matrix is trimethyl aminomethyl crosslinked agarose, which is commercially available, e.g., Q-Sepharose Fast Flow® (Pharmacia). Generally known commercially available cation exchange supports that may be used in the purification of proteins bear acidic functionalities, including carboxy and sulfonic acids. Matrices containing the cation functionalities include various forms of celluloses and polystyrene based matrices. For example, weak cation exchangers known in the art include, but are not limited to, Carboxymethyl-Sepharose® and Carboxymethyl-Cellulose®. Strong cation exchangers known in the art include, but are not limited to, sulfonated polystyrenes (AG 50W®, Bio-Rex 70®), sulfonated celluloses (SP-Sephadex®), and sulfonated Sepharoses (S-Sepharose®). A particularly preferred cation exchange matrix is S-Sepharose Fast Flow® (Pharmacia).

The chromatographic step involving these matrices is most preferably conducted as a column chromatography step or in alternative a batch absorptive technique, which optionally can be performed at a temperature between 25° C. to 40° C. Preferably, a salt is added to a washing or eluting buffer to increase the ionic strength of the buffer. Any of the salts conventionally used may be employed for this purpose as can be readily determined by one skilled in the art, with NaCl being one of the most frequently and conveniently used salts.

A conventional gel filtration step can also be used in combination with the HCIC or HIC chromatography process step. Representative examples of these matrices are polydextrans cross linked with acrylamides, such as composite hydrophilic gels prepared by covalently cross linking allyl dextran with N,N'-methylene bisacrylamide and crosslinked cellulose or agarose gels. Commercially available crosslinked dextran-acrylamides are known under the trade name Sephacryl® and are available from Pharmacia. Commercially available crosslinked dextran-agarose resins are known under the trade name Superdex®, available from Pharmacia. A preferred Superdex® gel is Superdex 200®. Examples of crosslinked cellulose gels are those commercially available cross linking porous cellulose gels, e.g., GLC 300® or GLC 1,000® that are available from Amicon Inc. Silica based resins such as TSK-Gel SW®, available from TosoHaas can be utilized. Polymer based resins such as TSK-Gel PW®, TSK Alpha Series®, Toyopearl HW Packings® (copolymerization of ethylene glycol and methyl acrylate polymers) are also available from TosoHaas.

Preferably, HCIC or HIC can be combined with one or more of these ion exchange steps. When a combination of HCIC or HIC and various ion exchange or gel filtration steps are used, they can be performed in any order. For example, as described below a four step procedure can be followed which includes HCIC using MEP Hypercel® chromatography or HIC using MacroPrep Methyl® chromatography, then Q Sepharose Fast Flow®, SP Sepharose Fast Flow® and lastly Superdex 200®. Several of these procedures are set forth in more detail below.

MEP Hypercel Chromatography

MEP (mercaptoethylpyridine) Hypercel® (BioSepra, Life Technologies) can be used for HCIC. It is a resin consisting of NEP linked to a regenerated cellulose bead of high porosity (80-100 microns). The functional group (MEP), consisting of a hydrophobic tail and an ionizable head group, is uncharged at neutral pH and can bind certain protein ligands based on hydrophobic interaction at a physiological ionic strength. Elution is accomplished by decreasing pH to 4 to 5, at which MEP is positively charged, and the protein elutes from the column due to electrostatic repulsion. For example, prepared harvest or harvest concentrate can be applied directly to the MEP column equilibrated with 25 mM sodium phosphate, pH 6.8, containing 180 mM sodium chloride and 2 mM DTT. Optionally, the column can then be washed with equilibration buffer containing 25 mM sodium caprylate until the absorbance at 280 nm (A280) stabilizes. The hmGCB can be eluted from the column with 50 mM sodium acetate, 2 mM DTT, pH 4.7, and the peak as monitored at 280 nm can be collected.

MacroPrep Methyl Chromatography

An alternative to MEP Hypercel® is MacroPrep Methyl®, which is a hydrophobic interaction chromatography (HIC) resin. This resin consists of a methyl functional group attached to a bead composition of macroporous co-polymerized glycol methacrylate and diethylene glycol dimethacrylate. For example, MacroPrep Methyl® (Bio-Rad) chromatography can be performed as follows. The pH of the harvest or harvest concentrate is adjusted to 5.6, and ammonium sulfate is added to 0.70 M final concentration.

The prepared harvest can be applied to the MacroPrep Methyl® column, which has been equilibrated in 0.70 M ammonium sulfate, 10 mM MES, pH 5.6. After application of the load, the column is washed with equilibrated buffer until the A280 returns to baseline. The hmGCB can be eluted with 10 mM MES, pH 5.6. The eluted hmGCB can be ultrafiltered and/or diafiltered in preparation for steps such as an ion exchange step such as Q Sepharose chromatography, SP Sepharose chromatography and/or Superdex 200 Chromatography.

Q Sepharose Chromatography

Q Sepharose Fast Flow® (Amersham Pharmacia) is a relatively strong anion exchange chromatography resin. The functional substitutent is a quaternary amine group, which is positively charged over the working pH range of 2 to 12. Proteins with a net negative charge at the working pH will tend to bind to the resin at a relatively low ionic strength and can be eluted at higher ionic strength or lower pH. HmGCB does not bind to Q Sepharose at approximately pH 6 and low ionic strength, but impurities do bind, thereby purifying the sample. For example, the following protocol can be used to purify hmGCB in the sample by Q Sepharose Fast Flow® chromatography. Under appropriate conditions, hmGCB flows through this column, so the product is found in the flowthrough/wash fraction. Sodium phosphate (250 mM, pH 6) is added to the MEP elution pool prepared as described above to a final concentration of 25 mM, and the pH of the pool is adjusted to pH 6 with NaOH (and HCl if necessary). The conductivity is adjusted to 2.5±0.1 mS/cm by dilution with water or by ultrafiltration/diafiltration using 25 mM sodium phosphate, 2 mM DTT, at approximately pH 6. The material is then filtered and applied to a column of Q Sepharose Fast Flow® which has been equilibrated in 25 mM sodium phosphate, 2 mM DTT, pH 6.0. After application of the load, the column is washed with equilibration buffer until the A280 reaches baseline. The flowthrough/wash fraction can then be processed through another column, e.g., SP Sepharose Fast Flow® column, shortly thereafter, e.g., within 24 hours, or frozen and stored at about −20° C. to −80° C. prior to further processing.

Other strong anion exchange resins, such as Macro-Prep High Q Support® (BioRad) can be used in place of Q Sepharose. A weaker anion exchange resin such as DEAE Sepharose Fast Flow® (Pharmacia) or Macro-Prep DEAE® (BioRad) can also be used. The column is equilibrated in buffer, e.g., 25 mM sodium phosphate, pH 6. The pH of the sample is adjusted to pH 6 and the conductivity is adjusted by dilution or diafiltration to a relatively low ionic strength, which allows impurities to bind to the column and hmGCB to flow through. The sample is applied and the column is washed with equilibration buffer. Impurities are still bound to the column, and can be eluted with application of salt, e.g., sodium chloride or potassium chloride, or application of a lower pH buffer, or a combination of increased salt and lower pH.

The hmGCB can also be allowed to bind the anion exchange column during loading by decreasing the salt concentration in the load or by running the column at a higher pH, or by a combination of both decreased salt and higher pH.

SP Sepharose Chromatography

SP Sepharose Fast Flow® (Amersham Pharmacia) is a relatively strong cation exchange chromatography resin. The functional substitutent is a charged sulfonic acid group, which is negatively charged over a working pH range of 2 to 12. Proteins with a net positive charge at the working pH will tend to bind to the resin at a relatively low ionic strength and can be eluted at higher ionic strength or higher pH. HmGCB binds to SP Sepharose at approximately pH 6 and intermediate ionic strength (e.g., 6.5 mS/cm) and can be eluted at higher ionic strength (e.g., 10.7 mS/cm). Impurity proteins remain bound to SP Sepharose under conditions of hmGCB elution, thereby purifying the hmGCB in the sample. For example, the following protocol can be used to purify hmGCB by SP Sepharose Fast Flow® chromatography. Sodium chloride (2.0 M stock) is added to the Q Sepharose® flowthrough/wash until the conductivity is 6.3 mS/cm. The pH is checked and readjusted to pH 6.0 if necessary. Then, addition of sodium chloride stock is continued until the conductivity is 6.5 mS/cm. The material is filtered and applied to a column of SP Sepharose Fast Flow®, which has been equilibrated with 25 mM sodium phosphate, 44 mM sodium chloride, pH 6.0. After application of the load, the column is washed with equilibration buffer until the baseline is reached and eluted with 25 mM sodium phosphate, 84 mM sodium chloride, pH 6.0. HmGCB is found in the elution fraction.

Another cation exchange resin, e.g., Source 30S® (Pharmacia), CM Sepharose Fast Flow® (Pharmacia), Macro-Prep CM Support® (BioRad) or Macro-Prep High S Support® (BioRad), can be used as an alternative to SP Sepharose. The hmGCB can bind to the column at approximately pH 6 and low to intermediate ionic strength, such as 4 to 7 mS/cm. A buffer, e.g., 10 mM sodium citrate, pH 6.0, 10 mM MES, pH 6.0, 25 mM sodium phosphate, pH 6.0, or other buffer with adequate buffering capacity at pH 6.0 can be used to equilibrate the column. The ionic strength of the sample is adjusted by dilution or diafiltration to a level which will accommodate binding to the column. The sample is applied to the column and the column is washed after the load to remove unbound material. A salt, e.g., sodium chloride or potassium chloride, can be used to elute the hmGCB from the column. Alternatively, the hmGCB can be eluted from the column with a buffer of higher pH or a combination of higher salt concentration and higher pH.

The hmGCB can also be made to flow through the cation exchange column during loading by increasing the salt concentration in the equilibration buffer and in the sample load, by running the column at a higher pH or by a combination of both increased salt and higher pH.

Superdex 200 Chromatography

Superdex 200 prep Grade® (Amersham Pharmacia) is used for size exclusion chromatography of hmGCB, whereby molecules are separated by size, molecular mass, strokes radius or hydrodynamic volume. Superdex 200 is composed of dextran covalently cross linked to agarose and has a fractionation range of 10,000 to 60,000 molecular weight for globular proteins. For example, the following protocol can be used to purify hmGCB by Superdex 200® chromatography. The SP elution pool is concentrated by ultrafiltration using a 10,000 mw cutoff membrane. The concentrated pool is filtered, then applied to a Superdex 200 prep Grade® column which has been equilibrated in 50 mM sodium citrate, pH 6.0. The A280 of the column effluent in the initial fractions is collected and, for example, an 8 to 16% SDS polyacrylamide gel is run to determine pooling of fractions. Pooling may be decided based on visual inspection of the silver-stained gel.

Other size exclusion chromatography resins such as Sephacryl S-200 HR®, Bio-Gel A 1.5M®, or TosoHaas TSK Gel resins can also be used to purify hmGCB. The buffer used for size exclusion chromatography of hmGCB is 50 mM sodium citrate, pH 6.0. Other buffers can also be used such as 25 mM sodium phosphate, pH 6.0 containing 0.15

M sodium chloride. The pH of the buffer can be between pH 5 and pH 7 and should have sufficient ionic strength to minimize ionic interactions with the column.

Variations of pH, buffer and/or salt concentration in any of the purification protocols described above can be performed by routine methods to achieve the desired purified product.

Assays for Determining Macrophage Uptake and Cellular Targeting of hmGCB

The uptake efficiency of hmGCB by macrophages can be determined by assaying, e.g., protein levels and/or enzyme activity in macrophages. For example, as described in the Examples below and in Diment et al. (1987) *J. Leukocyte Biol.* 42:485-490, an in vitro assay using a macrophage cell line can be used to determine absolute and mannose receptor specific uptake of hmGCB.

In addition, in vivo comparison of uptake of hmGCB and GCB by liver cells can be determined as described, for example, in Friedman et al. (1999) *Blood* 93:2807-2816. Briefly a mouse model can be injected with hmGCB or GCB, and then sacrificed shortly thereafter. The liver of the animal can then be used to prepare a suspension of liver cells, e.g., parenchymal cells, Kupffer cells, endothelial cells and hepatocytes. The cells can then be separated, identified by morphology and the protein levels and/or enzymatic activity of hmGCB and GCB in the various liver cell types can be determined. Alternatively, immunohistochemical detection maybe be used to localize hmGCB to a specific cell or cell type in tissue of treated animals.

Pharmaceutical Compositions

High mannose glucocerebrosidase (hmGCB) can be incorporated into pharmaceutical compositions suitable for administration to a subject, e.g., a human. The composition can include a sufficient dosage of hmGCB to treat a subject having Gaucher disease. As used herein the language "pharmaceutically acceptable carrier" is intended to include any and all solvents, excipients, dispersion media, coatings, antibacterial and antifungal agents, isotonic and adsorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, and subcutaneous administration. Preferably, the route of administration is intravenous. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders, e.g., lyophilized preparations, for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged stability of the injectable compositions can be brought about by including in the composition an agent which delays adsorption, for example, aluminum monostearate, human serum albumin and gelatin.

Sterile injectable solutions can be prepared by incorporating the hmGCB in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, e.g., lyophilization, which yields a powder of the active ingredient plus any additional desired ingredient from a previously sterile-filtered solution thereof.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Treatment of Gaucher Disease

HmGCB, e.g., any hmGCB molecule or preparation described herein, can be used to treat a subject having Gaucher disease. Alternatively, any mannosidase knockout cell described herein, can be introduced into a subject having Gaucher disease to deliver hmGCB to the subject. Various routed of administration and various sites can be used. Once implanted in individual, the knockout cell can produce hmGCB.

Preferably, the knockout cells used will generally be patient-specific genetically engineered cells. It is possible, however, to obtain cells form another individual of the same species or form a different species. Use of such cells might require administration of an immunosuppressant, alteration of histocompatibility antigens, or use of a barrier device to prevent rejection of the implanted cells.

Gaucher disease is an autosomal recessive lysosomal storage disorder characterized by a deficiency in the lysosomal enzyme, glucocerebrosidase (GCB). GCB hydrolyzes the glycolipid glucocerebroside that is formed after degradation of glycosphingolipids in the membranes of white blood cells and red blood cells. If GCB hydrolysis is insufficient then glucocerebroside can accumulate in macrophages (Gaucher cells), causing anemia, thrombocytopenia, organomegaly and major bone problems.

There are several types of Gaucher disease including Gaucher type 1, type 2 and type 3, which can arise due to various mutations in the GCB gene. A "therapeutically effective amount" of hmGCB, i.e., a dosage of hmGCB sufficient to treat Gaucher disease, can be given to a subject having this disorder. The term "treat" as used herein refers to reducing or inhibiting one or more symptoms of Gaucher disease. Symptoms of Gaucher disease type I include: skeletal complications such as bone pain, bone lesions, osteopenia, osteonecrosis, avascular necrosis and pathological fractures; anemia; hepatosplenomegaly; splenic nodules and liver dysfunction; thrombocytopenia; and/or delayed growth and pubertal development. Symptoms of Gaucher disease type II include the symptoms of Gaucher type I as well as neck rigidity, apathy, catatonia, strabismus, increased deep reflex and laryngeal spasm. Symptoms of Gaucher disease type III are similar to Gaucher type II except milder and later in onset.

A therapeutically effective amount of hmGCB can be determined on an individual basis and will be based, at least in part, on consideration of the size of the patient, the agent used, the type of delivery system used, the time of administration relative to the severity of the disease, and whether a single, multiple, or a controlled release dose regimen is employed. Preferably, the dosage of hmGCB sufficient to treat Gaucher disease is less than the dosage of human tissue derived or human placenta derived GCB, or GCB produced by cells in vitro and then trimmed to expose core mannose residues.

Treatment of Other Lysosomal Storage Diseases

Generally, the invention described herein can be used to produce proteins for targeting any cells that express mannose receptors on their surface. Thus, the invention described herein can be used to treat any disorder in which it is desirable to target a protein for treatment to a mannose receptor-expressing cell. For example, the invention described herein can also be applied to other lysosomal storage enzymes and other lysosomal storage diseases in which cells, e.g., the cells of reticuloendothelial origin, accumulate undigested substrate. Reticuloendothelial cells include macrophages, Kupffer cells in the liver and histiocytes in the spleen. Such lysosomal storage diseases include, but are not limited to, Farber disease and Neimann-Pick disease.

Farber disease is an autosomal recessive lysosomal storage disorder characterized by a deficiency in acid ceramidase. Ceramidases are enzymes responsible for degradation of ceramide. If ceramide degradation is insufficient then ceramide accumulates leading to granuloma formation and histiocytic response. (Moser, H. W. Ceramidase deficiency: Farber lipogranulomatosis; In: The Metabolic and Molecular Basis of Inherited Disease (C. R. Scriver, A. L. Beaudet, W. S. Sly and D. Valle, Eds.), Seventh edition, pp. 2589-2599, McGraw-Hill Inc., New York (1995))

There are several types of Farber disease including Farber type 1, type 2, type 3, type 4, and type 5 which differ in severity and sites of major tissue involvement. There is also type 6 and type 7 Farber disease. High mannose acid ceramidase can be given to a subject having Farber disease to treat, i.e., alleviate or reduce at least one symptom, of the disease. Symptoms of Farber disease type 1 include: swelling of the joints (particularly the interphalangeal, metacarpal, ankle, wrist, knee and elbow), palpable nodules in relation to the affected joints and over pressure points, a hoarse cry that may progress to aphonia, feeding and respiratory difficulty, poor weight gain and intermittent fever. The symptoms usually occur between ages two weeks and four months. Symptoms of Farber type 2 and type 3 include: subcutaneous nodulaes, joint deformities, and laryngeal involvement. These subjects survive longer than subjects having Farber type 1. Farber disease type 5 symptoms include psychomotor deterioration beginning at one to two and half years of age.

Neimann-Pick disease type A and type B are an autosomal recessive lysosomal storage disorder characterized by a deficiency acid sphingomyelinase. Acid sphingomyelinase is an enzyme responsible for degradation of sphingomyelin. If sphingomyelinase is deficient, sphingomyelin and other lipids can accumulate in the monocyte-macrophage system. (Schuman, E. H. and Desnick, R. J. Neimann-Pick Disease types A and B: acid sphingomyelinase deficiencies; In: The Metabolic and Molecular Basis of Inherited Disease (C. R. Scriver, A. L. Beaudet, W. S. Sly and D. Valle, Eds.), Seventh edition, pp. 2589-2599, McGraw-Hill Inc., New York (1995))

There are several types of Neimann-Pick disease including type A and type B. High mannose acid sphingomyelinase can be given to a subject having Neimann-Pick disease to treat, i.e., alleviate or reduce at least one symptom, of the disease. Symptoms of Neimann-Pick disease type A include: enlargement of the spleen and liver, lymphadenopathy, microcytic anemia, decreased platelet count, hypotonia, muscular weakness, psychomotor retardation. Symptoms of Neimann-Pick type B include: enlargement of the liver and/or spleen, heptoslenomegaly; pulmonary compromise.

Thus, high mannose lysosomal storage enzymes such as high mannose acid ceramidase or high mannose acid spingomyelinase can be produced by the methods described herein in order to target these proteins to mannose receptor-expressing cells.

Examples

In experiments with HT-1080 cells expressing Gene-Activated™ GCB (GA-GCB), the cells were treated with either kifunensine or swainsonine at concentrations ranging from 0.1 to 2 µg/mL.

Effect of Kifunensine or Swainsonine on GA-GCB Glycoforms

HT-1080 cells producing GA-GCB were plated in duplicate 6-well plates and the Production Medium adjusted to the following concentrations of kifunensine or swainsonine: 0 (no drug), 0.1, 0.25, 0.5, 1, and 2 µg/mL. The medium was harvested and the cells refed every 24 hours for three days. The samples from the third day were subjected to isoelectric focusing (IEF) analysis. The effect of kifunensine and swainsonine on the molecular charge of GA-GCB is shown by the IEF analysis. With both drugs, a concentration dependent increase in the apparent isoelectric point (pI) was observed, with kifunensine causing a much larger shift in pI than swainsonine at the highest concentration tested (2 µg/mL).

Effect of Kifunensine or Swainsonine on GA-GCB Production

Ten roller bottles (surface area, 1700 cm$^2$ each) were seeded in Growth Medium (DMEM with 10% calf serum) with HT-1080 cells producing GA-GCB. Following two weeks of growth, the medium was aspirated and 200 mL of fresh Production Medium (DMEM/F12, 0% calf serum) was added to three sets of roller bottles. Two sets of 4 roller bottles were treated with 1 µg/mL of either kifunensine or swainsonine. The third group of two roller bottles received no drug treatment. After approximately 24 hours, the medium from each roller bottle was harvested, pooled and a sample taken for GA-GCB enzymatic activity analysis. This procedure was repeated for seven days. Stable production of GA-GCB was observed for all roller bottles throughout the seven daily harvests (Table 1). Absolute levels of the enzyme, however, varied according to drug treatment group with the following average GA-GCB production levels observed across the seven harvests: 38.3±3.5 mg/L (control, no drug treatment), 24.5±4.0 mg/L (swainsonine, 1 µg/mL), and 21.3±2.8 mg/L (kifunensine, 1 µg/mL). Both drugs, therefore, resulted in stable, but lower production levels with the largest decrease seen for kifunensine (44% reduction relative to control).

cells was 14-fold over background and 73% inhibitable by mannan and that uptake of GA-GCB from swainsonine treated cells was 7-fold over background and 67% inhibitable by mannan. In addition, they also demonstrate that uptake of GA-GCB from untreated cells was approximately 3-fold over background and 53% inhibitable by mannan. Thus, the inhibition of intracellular mannosidases by either kifunensine or swainsonine results in GA-GCB that can be transported into cells efficiently via the mannose receptor, with kifunensine causing an approximately 2-fold greater uptake than swainsonine. Improvement in targeting of GA-GCB to cells via mannose receptors can therefore be optimized by production of GA-GCB in the presence of kifunensine or swainsonine.

TABLE 1

Roller Bottle Production of Glucocerebrosidase in Cells Treated with Mannosidase Inhibitors

| | Glucocerebrosidase[a)] Activity ([b)] (mg/Liter) | | | | | | | |
|---|---|---|---|---|---|---|---|---|
| Treatment | Harvest 1 | Harvest 2 | Harvest 3 | Harvest 4 | Harvest 5 | Harvest 6 | Harvest 7 | Average ± Standard Deviation |
| No drug added | 35.8 | 36.6 | 44.9 | 40.5 | 34.6 | 38.3 | 37.2 | 38.3 ± 3.5 |
| Swainsonine (1 μg/ml) | 28.6 | 17.4 | 28.5 | 27.0 | 22.9 | 25.0 | 22.3 | 24.5 ± 4.0 |
| Kifunensine (1 μg/ml) | 26.0 | 22.9 | 17.7 | 21.2 | 18.4 | 21.0 | 22.0 | 21.3 ± 2.8 |

[a)]Assay performed as follows: test article is mixed with the enzyme substrate (4-methylumbelliferyl-β-D-glucopyranoside) and incubated for 1 hour at 37° C. The reaction is stopped by the addition of NaOH/Glycine buffer. Fluorescence is quantified by the use of a fluorescence spectrophotometer.
[b)]Specific activity: 2,500 Units/mg. One unit is defined as the conversion of 1 μMole of substrate in 1 hour at 37° C.

Effect of Kifunensine or Swainsonine on GA-GCB Uptake into Macrophages

GA-GCB produced in HT-1080 cells was used in an in vitro assay to determine uptake efficiency in a mouse macrophage cell line. The specific objective of the experiment was to determine the absolute and mannose receptor-specific uptake of GA-GCB in mouse J774E cells. One day prior to assay, J774E cells were plated at 50,000 cells/cm$^2$ in 12 well plates in Growth Medium. For the assay, 0.5 mL of Production Medium (DMEM/F12), 0% calf serum) containing 50 nM vitamin D3 (1,2-5, Dihydroxy vitamin D3) was added to the cells. Unpurified GA-GCB (from harvest 4, Table 1) was added to the test wells at a final concentration of 10 μg/mL in the presence or absence of 2 μg/mL mannan (a competitor for the mannose receptor). Three different forms of GA-GCB were used: GA-GCB from cells treated with kifunensine (1 μg/mL), GA-GCB from cells treated with swainsonine (1 μg/mL), and GA-GCB (1 μg/mL) from untreated cells. Control wells received no GA-GCB. The wells were incubated for 4 hours at 37° C., then washed extensively in buffered saline, scraped into GA-GCB enzyme reaction buffer, passed through 2 freeze/thaw cycles, and clarified by centrifugation. The supernatant was then quantitatively tested for enzyme activity and total protein. Internalization of GA-GCB into mouse J744E cells is shown in Table 2 and is reported as Units/mg of cell lysate. These results demonstrated that uptake of GA-GCB from kifunensine treated

TABLE 2

Internalization of Glucocerebrosidase Into J774E Cells. Glucocerebrosidase Produced from Cells Treated with Mannosidase Inhibitors

| | [a)] Glucocerebrosidase Activity (Units/mg cell lysate) | | |
|---|---|---|---|
| [b)] Sample | Absolute | Background Corrected | Inhibition (%) |
| Background (no GA-GCB added) | 655 | 0 | — |
| GA-GCB from untreated cells | 2816 | 2161 | — |
| +Mannan | 1678 | 1023 | 53 |
| GA-GCB from kifunensine treated cells | 9185 | 8530 | — |
| +Mannan | 2977 | 2322 | 73 |
| GA-GCB from swainsonine treated cells | 4787 | 4132 | — |
| +Mannan | 2036 | 1381 | 67 |

[a)] Assay performed as follows: sample is mixed with the enzyme substrate (4-methylumbelliferyl-β-D-glucopyranoside) and incubated for 1 hour at 37° C. The reaction is stopped by the addition of NaOH/Glycine buffer. Fluorescence is quantified by the use of a fluorescence spectrophotometer.Total protein determined in freeze/thaw cell lysates by bicinchoninic acid (BCA). Activity reported as units/mg total protein. One Unit is defined as the conversion of 1 μMole of substrate in 1 hour at 37° C.
[b)] Cells treated with drug received 1 μg/mL of either Kifunensine or Swainsonine in the presence or absence of mannan (2 μg/mL).

Purification and Characterization of hmGCB

HmGCB was purified from the culture medium of human fibroblasts grown in the presence of kifunensine at a concentration of 2 μg/ml. The four N-linked glycans present on hmGCB were released by peptide N-glycosidase F and purified using a Sep-pak C18 cartridge. Oligosaccharides eluting in the 5% acetic acid fraction were permethylated using sodium hydroxide and methyl iodide, dissolved in methanol:water (80:20), and portions of the permethylated glycan mixture were analyzed by matrix-assisted laser desorption ionization time-of-flight mass spectroscopy (MALDI-TOF-MS). The sample was analyzed on a Voyager STR Biospectrometry Research Station laser-desorption mass spectrometer coupled with Delayed Extraction using a matrix of 2, 5-dihydroxybenzoic acid. A pattern of pseudo-molecular ions is seen in the range m/z 1500-2500, indicating the presence of high-mannose glycans ranging from $Man_5GlcNAc_2$ to $Man_9GlcNAc_2$.

TABLE 3

Summary of Data Obtained from MALDI-TOF-MS Analysis of N-Glycans from hmGCB from Kifunensine-Treated Cells

| M/Z | Peak Assignment | Approximate % of Total Glycans |
|---|---|---|
| 1580 | $Man_5GlcNAc_2$ | 1.3 |
| 1730 | $Man_6GlcNAc_2$ | 11.2 |
| 1752 | | |
| 1784 | | |
| 1934 | $Man_7GlcNAc_2$ | 23.3 |
| 1957 | | |
| 1988 | | |
| 2139 | $Man_8GlcNAc_2$ | 32.0 |
| 2161 | | |
| 2192 | | |
| 2343 | $Man_9GlcNAc_2$ | 31.2 |
| 2365 | | |
| 2397 | | |
| 2969 | Biantennary complex | 1.0 |

The most abundant high mannose glycans present are $Man_9GlcNAc_2$ and $Man8GlcNAc_2$, with decreasing abundances of $Man_7GlcNAc_2$, $Man_6GlcNAc_2$, and $Man_5GlcNAc_2$. A trace amount of a fucosylated biantennary complex glycan containing two sialic acid residues was observed. An approximate indication of the relative abundancy of each glycan is obtained by measuring the peak heights. See Table 3. A more accurate assessment of the average chain length of the high mannose glycans was obtained by MALDI-TOF-MS analysis of the intact glycoprotein. A sharp peak was obtained at m/z 62,483.1 due to the homogeneity of the glycan chains. The mass of the mature peptide calculated from the amino acid sequence is 55,577.6, indicating the four N-linked glycan chains contribute 6905.5 to the total mass of hmGCB. From this number, it can be calculated that the average glycan length is 8.15 mannose residues.

All patents and references cited herein are incorporated in their entirety by reference.

Other embodiments are within the following claims.

What is claimed:

1. A method of treating a subject having Gaucher disease, the method comprising:
   administering to the subject a pharmaceutical composition comprising a high mannose glucocerebrosidase (hmGCB) preparation in an amount suitable for treating Gaucher disease, wherein at least 90% of the hmGCB in the preparation comprise at least one carbohydrate chain that comprises six or more mannose residues from a precursor oligosaccharide, to thereby treat the subject,
   wherein the hmGCB preparation is produced by a process comprising
   (i) providing a mammalian cell which is capable of expressing human glucocerebrosidase (GCB), wherein the GCB comprises a precursor oligosaccharide that comprises a pentasaccharide core;
   (ii) contacting the cell with kifunensine such that the removal of at least one mannose residue distal to the pentasaccharide core of the precursor oligosaccharide of GCB is prevented;
   (iii) allowing the cell to produce hmGCB; and
   (iv) harvesting the hmGCB from the cell or its culture media.

2. The method of claim 1, wherein the kifunensine is present at a concentration between 0.05 to 20.0 µg/ml.

3. The method of claim 2, wherein the kifunensine is present at a concentration between 0.1 to 2.0 µg/ml.

4. The method of claim 1, wherein the composition comprises a hmGCB that has at least one carbohydrate chain having five mannose residues.

5. The method of claim 1, wherein the composition comprises a hmGCB that has at least one carbohydrate chain having nine mannose residues.

6. The method of claim 1, wherein at least 20% of the hmGCB of the preparation have one or more carbohydrate chains having at least eight mannose residues.

7. The method of claim 6, wherein at least 40% of the hmGCB of the preparation have one or more carbohydrate chains having at least eight mannose residues.

8. The method of claim 7, wherein at least 60% of the hmGCB of the preparation have one or more carbohydrate chains having at least eight mannose residues.

9. The method of claim 1, wherein at least 80% or more of the carbohydrate chains of the hmGCB of the preparation have six or more mannose residues.

10. The method of claim 1, wherein the cell comprises an exogenous nucleic acid comprising a GCB coding region.

11. The method of claim 10, wherein the cell further comprises an exogenous regulatory element which functions to regulate expression of the GCB coding region.

12. The method of claim 1, wherein the cell is a human cell that comprises an exogenous regulatory element which functions to regulate expression of an endogenous GCB gene.

13. The method of claim 1, wherein the cell is a primary cell.

14. The method of claim 1, wherein the cell is a secondary cell.

15. The method of claim 1, wherein the cell is a human cell.

16. The method of claim 15, wherein the cell is a fibroblast or a myoblast.

17. The method of claim 16, wherein the cell is an HT-1080 cell.

18. The method of claim 15, wherein the cell is an immortalized cell.

19. The method of claim 1, wherein the composition is administered by a parenteral route.

20. The method of claim 19, wherein the parenteral route is selected from the group consisting of: intravenous, intradermal, and subcutaneous administration.

21. The method of claim 20, wherein the composition is administered by intravenous administration.

22. The method of claim 1, wherein the Gaucher disease is Gaucher disease type I.

23. The method of claim 1, wherein the Gaucher disease is Gaucher disease type II.

24. The method of claim 1, wherein the Gaucher disease is Gaucher disease type III.

25. The method of claim 1, wherein the GCB in the preparation has a ratio of carbohydrate chains having five or more mannose residues to carbohydrate chains having four or less mannose residues which is about 80%:20%.

26. The method of claim 1, wherein the GCB in the preparation has a ratio of carbohydrate chains having five or more mannose residues to carbohydrate chains having four or less mannose residues which is about 85%:15%.

27. The method of claim 1, wherein the GCB in the preparation has a ratio of carbohydrate chains having five or more mannose residues to carbohydrate chains having four or less mannose residues which is about 90%:10%.

28. The method of claim 1, wherein the GCB in the preparation has a ratio of carbohydrate chains having five or more mannose residues to carbohydrate chains having four or less mannose residues which is about 95%:5%.

* * * * *

SEQUENCE LISTING

```
<160> NUMBER OF SEQ ID NOS: 2

<210> SEQ ID NO 1
<211> LENGTH: 8850
<212> TYPE: DNA
<213> ORGANISM: Homo sapiens

<400> SEQUENCE: 1
tctagaaaga cttcactgag atcatttaaa gaacaaaaag gatggctggg gtccagcgca      60
gtggctcatg cctgtaatcc cagcacttc ggataccaag gcagcagatc acctgaggtc     120
cagagtttca gaccagcctg gccaacatag tgaaacccca tctctactaa aaataaaaaa     180
attagctgag catgttggag ggcacctgta atcccagcta cttgggaggc tgaggcagga     240
gaatcactcg aacccaggag gtggaggttg cagtgagcca agatcacgcc actgcactcc     300
agcctgggca acagagtgag actctgtctc aaaaaacaac aacaacaaaa aatacaaaca     360
agagacaagt agttcccagg tgcctaccaa gtggtcaggc actgcactta cctcactgac     420
tgcagtaacc acccttgag gttgtggcat tgcctccatt ttccaggcaa ggaaatgggc     480
tgagagctgg gattagtcag gtcatgactg tgtgtgccac tcccgctaaa tctcatttga     540
tgtggttcat gaggccacac catggacagc ttcctccttg tgtccactga ggatatggct     600
ttgtacaaca ctttggtttt ttgaacgact ttacaaacct ccctgtcttg tgaggaagga     660
agaacagtta ttaccatctg catctgatga tgaaacaagg gacgctgcag aggagccgca     720
ctgaccactc cctccctcca gtcctgtcat cccactgcca gtgtcccacc ctcttgtgcc     780
ctgcacttca ctggctaata accccctca ctttttcctc tgtgaagcca tcctggataa     840
ttccccaccc acgaatggtc cctcctcatc tcagagagct ctccatgcac acctgttacc     900
```

```
gtttctgtct ttatctgtaa atatctgtgt gtctgacttc catgcctcac acacctctat    960
agggcaaaga ctgtcttaaa catcttggta gtgtcagtat tttgcacagt gaagtttttt   1020
tttttaaatt atatcagctt tatttgtacc tttttgacat ttctatcaaa aaagaagtgt   1080
gcctgctgtg gttcccatcc tctgggattt aggagcctct accccattct ccatgcaaat   1140
ctgtgttcta ggctcttcct aaagttgtca cccatacatg ccctccagag ttttataggg   1200
catataatcg taacagatga gaggaagcca attgcccttt agaaatatgg ctgtgattgc   1260
ctcacttcct gtgtcatgtg acgctcctag tcatcacatg acccatccac atcgggaagc   1320
cggaattact gcagggcta acctagtgcc tatagctaag gcaggtacct gcatccttgt   1380
ttttgtttag tggatcctct atccttcaga gactctggaa ccctgtggt cttctcttca    1440
tctaatgacc ctgaggggat ggagttttca agtccttcca gagaggtaag agagagagct   1500
cccaatcagc attgtcacag tgcttctgga atcctggcac tggaatttaa tgaatgacag   1560
actctctttg aatccagggc catcatggct ctttgagcaa ggcacagatg gagggagggg   1620
tcgaagttga aatgggtggg aagagtggtg gggagcatcc tgatttgggg tgggcagaga   1680
gttgtcatca aagggttgc agggagagct gcacccaggt ttctgtgggc cttgtcctaa    1740
tgaatgtggg agaccgggcc atgggcaccc aaaggcagct aagccctgcc caggagagta   1800
gttgaggggt ggagaggggc ttgcttttca gtcattcctc attctgtcct caggaatgtc   1860
ccaagccttt gagtagggta agcatcatgg ctggcagcct cacaggattg cttctacttc   1920
aggcagtgtc gtgggcatca ggtgagtgag tcaaggcagt ggggaggtag cacagagcct   1980
cccttctgcc tcatagtcct ttggtagcct tccagtaagc tggtggtaga cttttagtag   2040
gtgctcaata aatccttttg agtgactgag accaactttg gggtgaggat tttgtttttt   2100
ttcttttgaa acagagtctt actctgttgc ctgggctgga gtgcagtggt gcaattttgg   2160
ctcattccaa cctctgcctc ccagattcaa gcgattctct tgcttcagct tcccaggtag   2220
ctgggattac aggcggccac cactacgccc agctaatttt tgtattttta gtagagacgg   2280
ggtttcacca tgctggcaag gcaggtctca aactcctcac ctcaggtgat ccgcccacct   2340
cggcctccta aagtgctagg attacaggtg tgagcccctg cgcccggcca aggggtgagg   2400
aattttgaaa ccgtgttcag tctctcctag cagatgtgtc cattctccat gtcttcatca   2460
gacctcactc tgcttgtact ccctcccctcc caggtgcccg cccctgcatc cctaaaagct   2520
tcggctacag ctcggtggtg tgtgtctgca atgccacata ctgtgactcc tttgaccccc   2580
cgacctttcc tgcccttggt accttcagcc gctatgagag tacacgcagt gggcgacgga   2640
tggagctgag tatggggccc atccaggcta atcacacggg cacaggtaac cattacaccc   2700
ctcacccccct gggccaggct gggtcctcct agaggtaaat ggtgtcagtg atcaccatgg   2760
agtttcccgc tgggtactga tacccttatt ccctgtggat gtcctcaggc ctgctactga   2820
ccctgcagcc agaacagaag ttccagaaag tgaagggatt tggagggcc atgacagatg    2880
ctgctgctct caacatcctt gccctgtcac cccctgccca aaatttgcta cttaaatcgt   2940
acttctctga agaaggtgag gaggaagggg acaagatgac atagagccat gaaaactttt   3000
cgttttttctt ttcttttttt aaatttttt tgaggcagaa tctcactctg cccattctgt    3060
cggcgagaca ggagtgcagt ggtgtgatct cccctcacag caacctctgc ctcccaggct   3120
atagtgattc tcctgcctca gcctcctgag tagctggaat tataggcgtg cgccactacc   3180
acctggctaa ttttttgtatt tttagtagag acagggtttc atcatgttga ccaggctagt   3240
cttaaactcc tgacctcaaa tgatatacct gccttggcct cccgaagtgc tggaattaca   3300
```

```
agtgtgagcc accgagccca gcagacactt ttctttttc tttttttttt tttgagacag    3360
agtctcgcac tgtcacccag gctggagtgc agtggcacaa tctcagctca ctgcaacctc    3420
cacctcccgg gttcaggtga ttctcctgtc tcagcctctc gagtacctgg gattacaggt    3480
gcctgccacc acgcccggct aatttttgt atttttagta gagacagggt ttcactatgt    3540
tggccaggat gattgcgaac tcctgacctc gtgatctgcc cacatcggcc tcccaaagtg    3600
ctgggattac atgcgtgagc cactgacact ttctttgcc ctttctttgg accctgactt    3660
ctgcccatcc ctgacatttg gttcctgttt taatgccctg tgaaataaga tttcgccgcc    3720
tatcatctgc taactgctac ggactcaggc tcagaaaggc ctgcgcttca cccaggtgcc    3780
agcctccaca ggttccaacc caggagccca agttcccttt ggccctgact cagacactat    3840
taggactggc aagtgataag cagagtccca tactctccta ttgactcgga ctaccatatc    3900
ttgatcatcc ttttctgtag gaatcggata taacatcatc cgggtaccca tggccagctg    3960
tgacttctcc atccgcacct acacctatgc agacaccccct gatgatttcc agttgcacaa    4020
cttcagcctc ccagaggaag ataccaagct caaggtaggc attctagctt tttcaggccc    4080
tgagggccct gatgtctggg ggttgagaaa ctgtagggta ggtctgcttg tacagacatt    4140
ttgtcccctg ctgttttgtc ctgggggtgg gagggtggag gctaatggct gaaccggatg    4200
cactggttgg gctagtatgt gttccaactc tgggtgcttc tctcttcact acctttgtct    4260
ctagataccc ctgattcacc gagccctgca gttggcccag cgtcccgttt cactccttgc    4320
cagcccctgg acatcaccca cttggctcaa gaccaatgga gcggtgaatg ggaaggggtc    4380
actcaaggga cagcccggag acatctacca ccagacctgg gccagatact ttgtgaagta    4440
agggatcagc aaggatgtgg gatcaggact ggcctcccat ttagccatgc tgatctgtgt    4500
cccaaccctc aacctagttc cacttccaga tctgcctgtc ctcagctcac ctttctacct    4560
tctgggcctt tcagccttgg gcctgtcaat cttgcccact ccatcaggct tcctgttctc    4620
tcggtctggc ccacttcctt tttattttc ttctttttt ttttttgag aaggagtctc    4680
tctctctgtc acccaggctg gagtgctgtg gcgccatctt cactcactgt aacctctgcc    4740
tcctgagttc aagcaattct cctgcctcag ccttccaagt agctgggatt ataggcgcct    4800
gccaccaggc ccagctgatt tttctatttt tagtagagac ggggtttcgc caggctgttc    4860
tcgaactcct gaactcaagt gatccacctg cctcggcttc ccaaagtgct gggattacag    4920
gtgtgagcca ccacacccag ctggtctggt ccactttctt ggccggatca ttcatgacct    4980
ttctcttgcc aggttcctgg atgcctatgc tgagcacaag ttacagttct gggcagtgac    5040
agctgaaaat gagccttctg ctgggctgtt gagtggatac ccttccagt gcctgggctt    5100
cacccctgaa catcagcgag acttcattgc ccgtgaccta ggtcctaccc tcgccaacag    5160
tactcaccac aatgtccgcc tactcatgct ggatgaccaa cgcttgctgc tgccccactg    5220
ggcaaaggtg gtaaggcctg gacctccatg gtgctccagt gaccttcaaa tccagcatcc    5280
aaatgactgg ctcccaaact tagagcgatt tctctaccca actatggatt cctagagcac    5340
cattcccctg gacctccagg gtgccatgga tcccacagtt gtcgcttgaa acctttctag    5400
gggctgggcg aggtggctca ctcatgcaaa cccagcactt tgggaagccg aggcgggtga    5460
tcacctgagg tcaggagttt aagaccaccc tggccaacgt gttgaaaccc tgtgtctact    5520
aaaatacaaa aaaaaaaaat tatctgggca tgatggtggg tgtctgtaat cccagctact    5580
caggaggctg agaagggaga atcagttgaa cccgggagat ggtggttgcg gtgagccgag    5640
```

```
atcgcgccac tgcactccag cctgggaggc tgagcgagac tccatctcga aacaaaacaa    5700
aacaaaacta tctaggctgg gggtggtggt tcatgtatgt atgtgtatat acatatatat    5760
gtgtttatat gtatatatat atacacacac acacatacat acacacacat acacacacaa    5820
attagctggg tgtggcaccc gtgtagtccc agctactcag gaggctaatg tgggaggatc    5880
agttgaccct aggaagtcaa ggctgcagtg agtcgtgatt gcgccactgt actccagccc    5940
gagtgacaga gtgacatcct gtctcaaaaa caaaaaaaaa tctccccaaa cctctctagt    6000
tgcattcttc ccgtcaccca actccaggat tcctacaaca ggaactagaa gttccagaag    6060
cctgtgtgca aggtccagga tcagttgctc ttcctttgca ggtactgaca gacccagaag    6120
cagctaaata tgttcatggc attgctgtac attggtacct ggactttctg gctccagcca    6180
aagccaccct aggggagaca caccgcctgt tccccaacac catgctcttt gcctcagagg    6240
cctgtgtggg ctccaagttc tgggagcaga gtgtgcggct aggctcctgg gatcgaggga    6300
tgcagtacag ccacagcatc atcacggtaa gccaccccag tctcccttcc tgcaaagcag    6360
acctcagacc tcttactagt ttcaccaaag actgacagaa gcccttcctg tccagctttc    6420
cccagctagc ctgcccttt gagcaactct ggggaaccat gattccctat cttccctttc    6480
cttcacaggt ctgcacacct cattgcccct tttgcaacta ctgaggcact tgcagctgcc    6540
tcagacttct cagctcccct tgagatgcct ggatcttcac acccccaact ccttagctac    6600
taaggaatgt gccctcaca gggctgacct acccacagct gcctctccca catgtgaccc    6660
ttacctacac tctctgggga ccccagtgt tgagcctttg tctctttgcc tttgtcctta    6720
ccctagaacc tcctgtacca tgtggtcggc tggaccgact ggaaccttgc cctgaacccc    6780
gaaggaggac ccaattgggt gcgtaacttt gtcgacagtc ccatcattgt agacatcacc    6840
aaggacacgt tttacaaaca gcccatgttc taccaccttg gccacttcag gtgagtggag    6900
ggcgggcacc cccattccat accaggccta tcatctccta catcggatgg cttacatcac    6960
tctacaccac gagggagcag gaaggtgttc agggtggaac ctcggaagag gcacacccat    7020
ccccttttgc accatggagg caggaagtga ctaggtagca acagaaaacc ccaatgcctg    7080
aggctggact gcgatgcaga aaagcagggt cagtgcccag cagcatggct ccaggcctag    7140
agagccaggg cagagcctct gcaggagtta tggggtgggt ccgtgggtgg gtgacttctt    7200
agatgagggt tcatgggag gtaccccgag ggactctgac catctgttcc cacattcagc    7260
aagttcattc ctgagggctc ccagagagtg gggctggttg ccagtcagaa gaacgacctg    7320
gacgcagtgg cactgatgca tcccgatggc tctgctgttg tggtcgtgct aaaccggtga    7380
gggcaatggt gaggtctggg aagtgggctg aagacagcgt tgggggcctt ggcaggatca    7440
cactctcagc ttctcctccc tgctccctag ctccctctaag gatgtgcctc ttaccatcaa    7500
ggatcctgct gtgggcttcc tggagacaat ctcacctggc tactccattc acacctacct    7560
gtggcgtcgc cagtgatgga gcagatactc aaggaggcac tggctcagc ctgggcatta    7620 aagggacaga gtcagctcac acgctgtctg tgactaaaga gggcacagca gggccagtgt    7680
gagcttacag cgacgtaagc ccaggggcaa tggtttgggt gactcacttt ccctctagg    7740 tggtgccagg ggctggaggc ccctagaaaa agatcagtaa gccccagtgt cccccagcc    7800 cccatgctta tgtgaacatg cgctgtgtgc tgcttgcttt ggaaactggg cctgggtcca    7860
ggcctagggt gagctcactg tccgtacaaa cacaagatca gggctgaggg taaggaaaag    7920
aagagactag gaaagctggg cccaaaactg gagactgttt gtctttcctg gagatgcaga    7980
actgggcccg tggagcagca gtgtcagcat cagggcggaa gccttaaagc agcagcgggt    8040
```

```
gtgcccaggc acccagatga ttcctatggc accagccagg aaaaatggca gctcttaaag      8100
gagaaaatgt ttgagcccag tcagtgtgag tggctttatt ctgggtggca gcaccccgtg      8160
tccggctgta ccaacaacga ggaggcacgg gggcctctgg aatgcatgag agtagaaaaa      8220
ccagtcttgg gagcgtgagg acaaatcatt cctcttcatc ctcctcagcc atgcccaggg      8280
tccgggtgcc tggggcccga gcaggcgttg cccgctggat ggagacaatg ccgctgagca      8340
aggcgtagcc caccatggct gccagtcctg ccagcacaga taggatctgg ttccggcgcc      8400
ggtatggctc ctcctcagtc tctgggcctg ctggtgtctg gcgttgcggt ggtacctcag      8460
ctgagggtca aggaaggaag gtgtgttagg agaactagtt cttggatccc tgcccactct      8520
ccccagggct gcccctccca tctgccccctt acctccatcc caggggaagt agagactgag      8580
aatgtgggta caataggcac agaggttgtg cagcccacgc aggtggacct gcagcttccc      8640
actgggcagc tttgcctgca gcagcagggc caagtagctg aagacgaagg cgtccaagga      8700
ggcagggctg gagcagagag agaagggtgg gatggaggag aaccactggg gtagaagggg      8760
taaagatgga gctggaggaa gagtcagcct tgggaggtgg gctctgggca gcaggcggcc      8820
accaggaagg acaggacaca cagttctaga                                       8850
```

<210> SEQ ID NO 2
<211> LENGTH: 536
<212> TYPE: PRT
<213> ORGANISM: Homo sapiens

<400> SEQUENCE: 2

```
Met Glu Phe Ser Ser Pro Ser Arg Glu Glu Cys Pro Lys Pro Leu Ser
  1               5                  10                  15

Arg Val Ser Ile Met Ala Gly Ser Leu Thr Gly Leu Leu Leu Leu Gln
             20                  25                  30

Ala Val Ser Trp Ala Ser Gly Ala Arg Pro Cys Ile Pro Lys Ser Phe
         35                  40                  45

Gly Tyr Ser Ser Val Val Cys Val Cys Asn Ala Thr Tyr Cys Asp Ser
     50                  55                  60

Phe Asp Pro Pro Thr Phe Pro Ala Leu Gly Thr Phe Ser Arg Tyr Glu
 65                  70                  75                  80

Ser Thr Arg Ser Gly Arg Arg Met Glu Leu Ser Met Gly Pro Ile Gln
                 85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220
```

-continued

```
Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
            245                 250                 255

Asp Ala Tyr Ala Glu His Lys Leu Gln Phe Trp Ala Val Thr Ala Glu
                260                 265                 270

Asn Glu Pro Ser Ala Gly Leu Leu Ser Gly Tyr Pro Phe Gln Cys Leu
            275                 280                 285

Gly Phe Thr Pro Glu His Gln Arg Asp Phe Ile Ala Arg Asp Leu Gly
        290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
                340                 345                 350

Leu Asp Phe Leu Ala Pro Ala Lys Ala Thr Leu Gly Glu Thr His Arg
            355                 360                 365

Leu Phe Pro Asn Thr Met Leu Phe Ala Ser Glu Ala Cys Val Gly Ser
        370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
            485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
530                 535
```